(12) United States Patent
Nakazawa et al.

(10) Patent No.: US 11,269,088 B2
(45) Date of Patent: Mar. 8, 2022

(54) RADIATION DETECTOR AND NUCLEAR MEDICINE DIAGNOSIS DEVICE

(71) Applicant: Shimadzu Corporation, Kyoto (JP)

(72) Inventors: Masayuki Nakazawa, Kyoto (JP); Tomoaki Tsuda, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 12 days.

(21) Appl. No.: 16/633,104

(22) PCT Filed: Jul. 31, 2017

(86) PCT No.: PCT/JP2017/027682
§ 371 (c)(1),
(2) Date: Jan. 22, 2020

(87) PCT Pub. No.: WO2019/026129
PCT Pub. Date: Feb. 7, 2019

(65) Prior Publication Data
US 2020/0233101 A1  Jul. 23, 2020

(51) Int. Cl.
*G01T 1/20* (2006.01)
*A61B 6/03* (2006.01)
*A61B 6/00* (2006.01)
*G01T 1/208* (2006.01)

(52) U.S. Cl.
CPC ............ *G01T 1/2006* (2013.01); *A61B 6/037* (2013.01); *A61B 6/4258* (2013.01); *A61B 6/485* (2013.01); *G01T 1/208* (2013.01)

(58) Field of Classification Search
CPC ..... G01T 1/2006; G01T 1/208; G01T 1/2985; A61B 6/037; A61B 6/4258; A61B 6/485; A61B 6/4233
See application file for complete search history.

(56) References Cited

U.S. PATENT DOCUMENTS

| | | | |
|---|---|---|---|
| 4,959,809 A * | 9/1990 | Rogers ................... | G01T 1/1644 250/363.01 |
| 6,348,692 B1 * | 2/2002 | Chapuis ................. | G01T 1/1642 250/369 |
| 7,019,297 B2 | 3/2006 | Aycak et al. | |
| 7,164,136 B2 | 1/2007 | Aycak et al. | |
| 9,903,960 B1 * | 2/2018 | Berker .................. | G01T 1/1642 |
| 2003/0116713 A1 * | 6/2003 | Cooke ................... | G01T 1/1647 250/369 |
| 2008/0164417 A1 * | 7/2008 | Hornig .................... | G01T 1/023 250/368 |

(Continued)

FOREIGN PATENT DOCUMENTS

JP  H02-078987 A  3/1990
JP  H11-023721 A  1/1999

OTHER PUBLICATIONS

Written Opinion by the International Search Authority for PCT application PCT/JP2017/027682, dated Oct. 24, 2017, submitted with a machine translation.

*Primary Examiner* — Marcus H Taningco
(74) *Attorney, Agent, or Firm* — Muir Patent Law, PLLC

(57) ABSTRACT

A radiation detector (5) is configured such that weighting of detection signals of photodetectors (52) on an end portion side of the plurality of photodetectors (52) is set to be greater than weighting of detection signals of photodetectors (52) on a central portion side of the plurality of photodetectors (52).

5 Claims, 18 Drawing Sheets

FIRST EMBODIMENT

(56) References Cited

U.S. PATENT DOCUMENTS

| | | | |
|---|---|---|---|
| 2011/0135179 A1* | 6/2011 | Ross | A61B 6/583 |
| | | | 382/131 |
| 2011/0192982 A1* | 8/2011 | Henseler | G01T 1/2008 |
| | | | 250/362 |
| 2014/0140469 A1* | 5/2014 | Carmi | A61B 6/4233 |
| | | | 378/9 |
| 2015/0338530 A1* | 11/2015 | Okada | H04N 5/361 |
| | | | 250/394 |
| 2017/0115409 A1* | 4/2017 | Laurence | G01T 7/005 |

* cited by examiner

FIRST EMBODIMENT

Comparative Example

Modification

RADIATION DETECTOR AND NUCLEAR MEDICINE DIAGNOSIS DEVICE

TECHNICAL FIELD

The present invention relates to a radiation detector and a nuclear medicine diagnostic device, and more particularly to a radiation detector and a nuclear medicine diagnostic device in which a plurality of photodetectors whose number is less than that of the plurality of scintillator elements is arranged.

BACKGROUND OF THE INVENTION

Conventionally, there has been known an array (radiation detector) in which photodetectors whose number is less than the number of a plurality of scintillator elements is arranged. Such an array is disclosed, for example, in U.S. Pat. No. 7,019,297.

The array described in the above-mentioned U.S. Pat. No. 7,019,297 is provided with a plurality of scintillator elements in which fluorescence is generated by incident gamma rays and photodetectors to which the plurality of scintillator elements is optically connected. The array is provided with a controller for specifying at which scintillator element among the plurality of scintillator elements connected to the photodetectors fluorescence is generated. Further, the array is provided with an optical barrier arranged between the plurality of scintillator elements to reflect fluorescence generated in the scintillator elements. The controller is configured to detect fluorescence generated and diffused in the scintillator element by the plurality of photodetectors and to specify the scintillator element in which the fluorescence is generated based on respective detection signals of the plurality of photodetectors.

Here, although not clearly described in the above-mentioned U.S. Pat. No. 7,019,297, fluorescence proceeding to an end portion among fluorescence generated in a scintillator element adjacent to a scintillator element arranged at the end portion (hereinafter referred to as "adjacent scintillator element) is reflected by the outer end surface portion of the scintillator element arranged at the end portion, and therefore the fluorescence tends to concentrate on the photodetector arranged at the end portion. Here, in the photodetector optically connected to the adjacent scintillator element in which fluorescence is generated, the photodetector receives the fluorescence in which the intensity is peak. However, since fluorescence tends to concentrate on the photodetector arranged at the end portion due to the reflection, the intensity of fluorescence received by the photodetector arranged at the end portion and the intensity of fluorescence received by the photodetector adjacent to the photodetector arranged at the end portion become close to each other. As a result, the strength of the detection signal detected in the photodetector arranged at the end portion and the strength of the detection signal detected in the photodetector adjacent to the photodetector arranged at the end portion become close. Therefore, the interval between the position where the fluorescence generated in the scintillator element arranged at the end portion is specified by the controller and the position where fluorescence generated in the scintillator element adjacent to the scintillator arranged the end portion is specified by the controller becomes smaller than the interval between the other specified positions. This makes it difficult to accurately specify the scintillator element in which the fluorescence is actually generated, in the case where the fluorescence generated in the scintillator element on the end portion side is specified by the controller and in the case where the fluorescence generated in the scintillator element adjacent to the scintillator element arranged at the end portion is specified by the controller.

Therefore, in the array described in the above-mentioned U.S. Pat. No. 7,019,297, by adjusting the length and the position of the optical partition wall to differentiate the intensity of the received fluorescence, the strength of the detection signal detected in the photodetector arranged at the end portion and the strength of the detection signal detected in the photodetector adjacent to the photodetector arranged at the end portion is differentiated. With this, the strength of the detection signal of the photodetector arranged at the end portion and the strength of the detection signal of the photodetector adjacent to the photodetector arranged at the end portion are differentiated from each other to specify the scintillator element in which fluorescence is actually generated.

PRIOR ART DOCUMENT

Patent Document

Patent Document 1: U.S. Pat. No. 7,019,297

SUMMARY OF THE INVENTION

Problems to be Solved by the Invention

However, in the configuration of the above-mentioned U.S. Pat. No. 7,019,297, in order to differentiate between the strength of the detection signal of the photodetector arranged at the end portion and the strength of the detection signal of the photodetector adjacent to the photodetector arranged at the end portion, it is required to adjust the lengths and the positions of the plurality of optical partition walls arranged between the plurality of scintillator elements. For this reason, in order to accurately specify the scintillator element in which fluorescence is generated, it takes time and labor for the adjustment to differentiate the strength of the detection signal of the photodetector arranged at the end portion and the strength of the detection signal of the photodetector adjacent to the photodetector arranged at the end portion in the array (radiation detector).

The present invention has been made to solve the aforementioned problems, and one of objects of the present invention is to provide a radiation detector and a nuclear medicine diagnostic device capable of easily performing an adjustment to differentiate between strength of a detection signal of a photodetector arranged at an end portion and strength of a detection signal of a photodetector adjacent to the photodetector arranged at the end portion in order to accurately specify a scintillator element in which fluorescence is generated.

Means for Solving the Problem

In order to achieve the aforementioned object, the radiation detector according to a first aspect of the present invention includes:

a scintillator in which a plurality of scintillator elements that convert radiation into fluorescence is arranged;

a plurality of photodetectors connected to the plurality of scintillator elements, the plurality of photodetectors whose number is less than a number of the plurality of scintillator elements being arranged, and each photodetector being configured to detect fluorescence generated in the scintillator element; and a controller configured to specify a generation position of the fluorescence based on signal values of the plurality of photodetectors, the signal values being obtained by weighting respective detection signals of the plurality of photodetectors, wherein weighting of the detection signal of the photodetector arranged on an end portion side between the plurality of photodetectors is set to be greater than weighting of the detection signals of photodetectors arranged on a central portion side between the plurality of photodetectors.

As described above, the radiation detector according to the first aspect of the present invention is provided with a plurality of photodetectors each configured to detect fluorescence generated in the scintillator element, and a controller configured to specify a generation position of the fluorescence based on signal values of the plurality of photodetectors, each of the signal values being weighted. The weighting of the detection signal of the photodetector arranged on the end portion side is set to be greater than the weighting of the detection signal of the photodetector arranged on the central portion side. With this, the difference between the strength of the weighted detection signal of the photodetector arranged on the end portion side and the strength of the weighted detection signal of the photodetector arranged at the central portion becomes greater than the difference between the strengths of the weighted detection signals of the photodetectors arranged on the central portion side. Therefore, it becomes possible to easily distinguish between the case in which the fluorescence is generated in the scintillator element arranged on the end portion side and the case in which the fluorescence is generated in the scintillator element arranged on the central portion side. As a result, in order to accurately specify the scintillator element in which fluorescence is generated, it becomes possible to easily perform an adjustment to differentiate between the strength of the detection signal of the photodetector arranged at the end portion and the strength of the detection signal of the photodetector adjacent to the photodetector arranged at the end portion without requiring labor, such as, e.g., an adjustment of a light partition wall or a light guide. In addition, since the strength of the detection signal of the photodetector arranged at the end portion and the strength of the detection signal of the photodetector adjacent to the photodetector arranged at the end portion can be differentiated without using an optical partition wall or a light guide, it is possible to suppress that the structure of the radiation detector becomes complicated.

In the radiation detector according to the first aspect, preferably, the weighting is based on a weighting ratio based on a difference between the signal values of weighted detection signals of the photodetectors arranged adjacently, and is set such that the weighting ratio at the end portion is greater than the weighting ratio on the central portion side. With this configuration, the difference in weighted signal value between the photodetector arranged at the end portion and the photodetector adjacent to the photodetector arranged at the end portion can be made greater than the difference in weighted signal value between the photodetectors arranged on the central portion side. This makes it easier to specify the position of the scintillator element in cases where fluorescence is generated in the scintillator element arranged on the end portion side, as compared with the case in which the weighting ratio is set equally between respective photodetectors.

In the radiation detector in which the weighting ratio at the end portion is set to be greater than the weighting ratio on the central portion side, preferably, a difference between the weighting ratio at the end portion and the weighting ratio on a most end portion side among the weighting ratios on the central portion side is set to be greater than differences between weighting ratios other than those at the end portion. With this configuration, it is possible to assuredly increase the difference between the weighted signal value of the photodetector arranged at the end portion and the weighted signal value of the photodetector adjacent to the photodetector arranged at the end portion, as compared with the difference between weighted signal values of photodetectors arranged on the central portion side. This makes it easier to specify the position of the scintillator element in cases where fluorescence is generated in the scintillator element arranged on the end portion side, as compared with the case in which the weighting ratio is set equally between the detectors.

In this case, preferably, the weighting ratio is set so that the difference between the weighting ratios other than those at the end portion is a constant value of 1 or 2. With this configuration, it is possible to differentiate between the weighted signal values of the photodetectors arranged on the central portion side. As a result, the difference between the weighted signal value of the photodetector arranged at the end portion and the weighted signal value of the photodetector adjacent to the photodetector arranged at the end portion is increased, so that it is possible to reduce that the difference between the weighted signal values of the scintillator elements arranged on the central portion side.

In the radiation detector in which the weighting is set based on the aforementioned weighting ratio, preferably, the radiation detector further includes a plurality of resistors for weighting respective detection signals output from the plurality of photodetectors, and resistance values of the plurality of resistors are adjusted based on the weighting ratio. With this configuration, it is possible to easily weight respective detection signals of the plurality of photodetectors.

In this case, preferably, the radiation detector further includes an adding circuit configured to add the weighted signal value to respective detection signals of the plurality of photodetectors, and the controller is configured to specify the generation position of the fluorescence based on the signal value added by the adding circuit. With this configuration, the scintillator element in which fluorescence is generated can be specified only by adding the signal value weighted by the adding circuit, so that the configuration of the radiation detector can be simplified.

In order to achieve the aforementioned object, the nuclear medicine diagnostic device according to the second aspect of the present invention includes:

a scintillator in which a plurality of scintillator elements that convert radiation emitted from a subject into fluorescence is arranged;

a plurality of photodetectors connected to the plurality of scintillator elements, the plurality of photodetectors whose number is less than a number of the plurality of scintillator elements being arranged, and each photodetector being configured to detect fluorescence generated in the scintillator element; and a controller configured to specify a generation position of the fluorescence based on signal values of the plurality of photodetectors, the signal values being obtained by weighting respective detection signals of the plurality of photodetectors, wherein weighting of the detection signal of the photodetector arranged on an end portion side between the plurality of photodetectors is set to be greater than weighting of the detection signals of photodetectors arranged on a central portion side between the plurality of photodetectors.

The nuclear medicine diagnostic device according to the second aspect of the present invention includes, as described above, a plurality of photodetectors for detecting fluorescence generated in the scintillator element and a controller for specifying the generation position of the fluorescence based on signal values obtained by weighting respective detection signals of the plurality of photodetectors. The weighting of the detection signals of the photodetectors arranged on the end portion side is set to be greater than the weighting of the detection signals of the photodetectors arranged on the central portion side. Thus, in order to accurately specify the scintillator element in which fluorescence is generated, it is possible to easily perform an adjustment for differentiating between the strength of the detection signals of photodetectors arranged at the end portion and the strength of detection signal of the photodetector adjacent to the photodetector arranged at the end portion without requiring labor, such as, e.g., an adjustment of a light partition wall or a light guide.

Effects of the Invention

According to the present invention, as described above, in order to accurately specify the scintillator element in which fluorescence is generated, it is possible to easily perform adjustments to differentiate between the strength of the detection signal of the photodetector arranged at the end portion and the strength of the detection signal of the photodetector adjacent to the photodetector arranged at the end portion.

Figure 3:
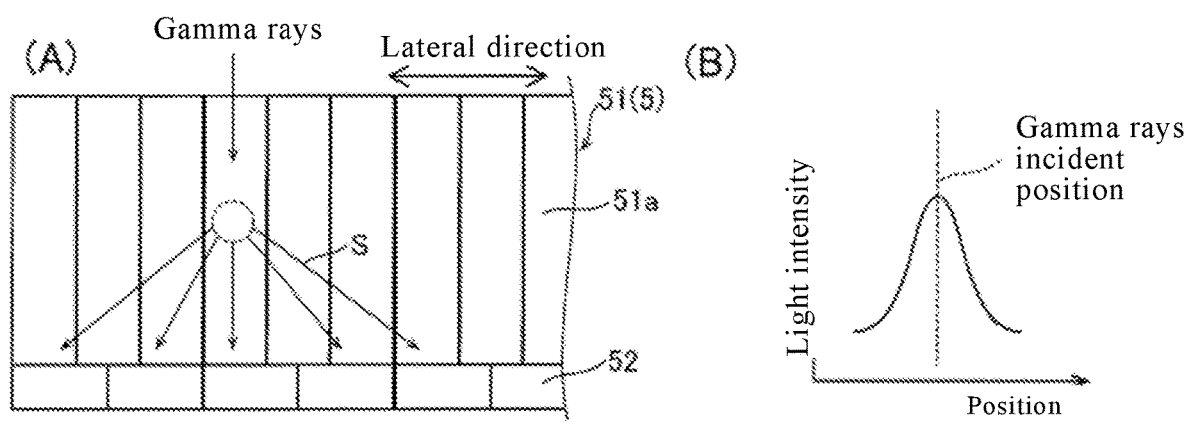

(A) of FIG. 3 is a cross-sectional view schematically showing a state in which gamma rays are incident on a scintillator element, and (B) of FIG. 3 is a graph schematically showing the relationship between the intensity and the position of the fluorescence generated in the scintillator element.

Figure 4:
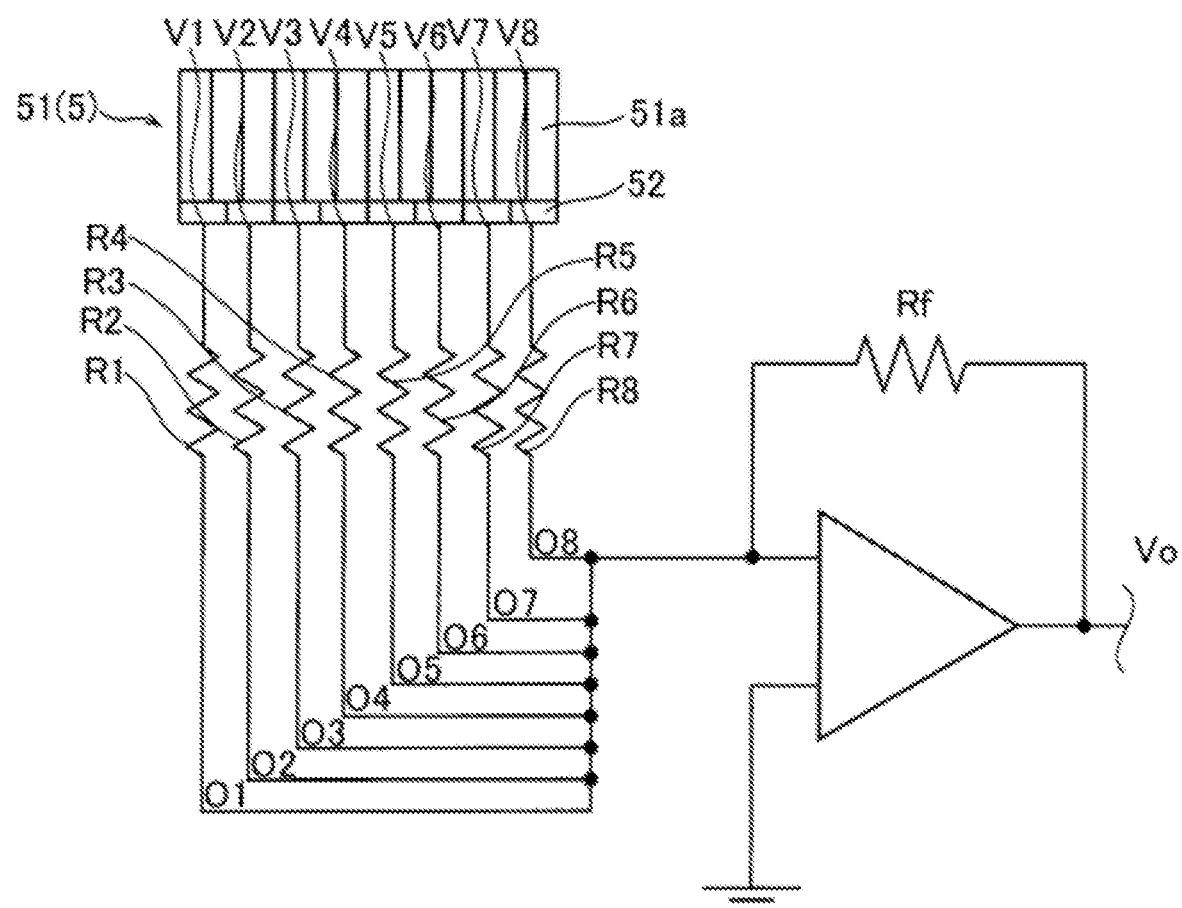

FIG. 4 is a circuit diagram schematically showing a weighting arithmetic circuit connected to photodetectors arranged in a lateral direction in a radiation detector according to the first embodiment of the present invention.

Figure 5:
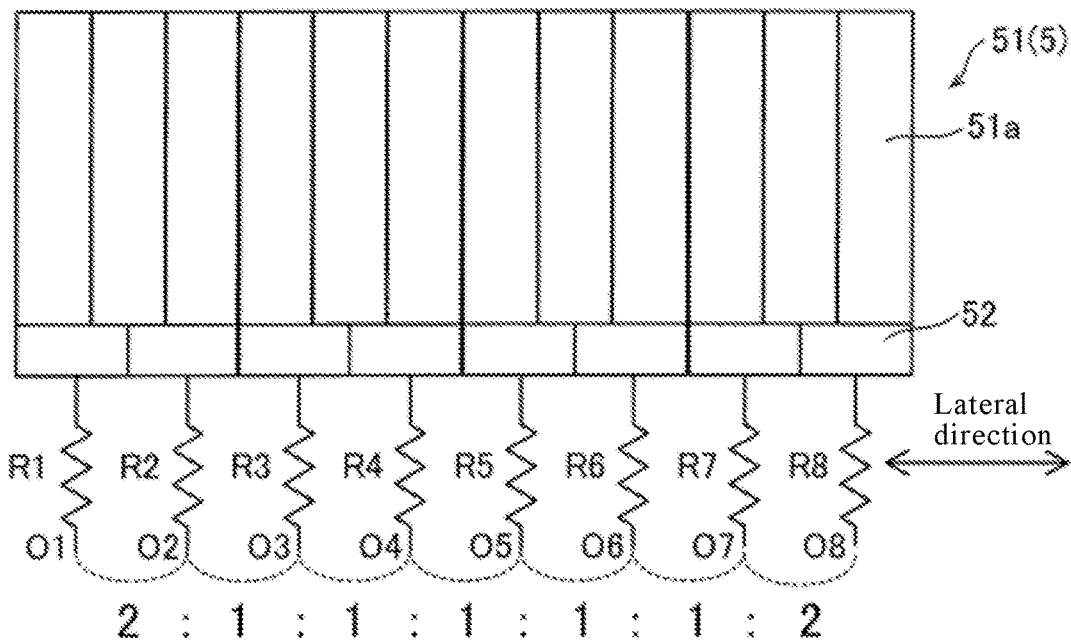

FIG. 5 is a circuit diagram in which resistors are connected to respective photodetectors arranged in a lateral direction such that weighting is increased at the end portion in the radiation detector according to the first embodiment of the present invention.

Figure 6:
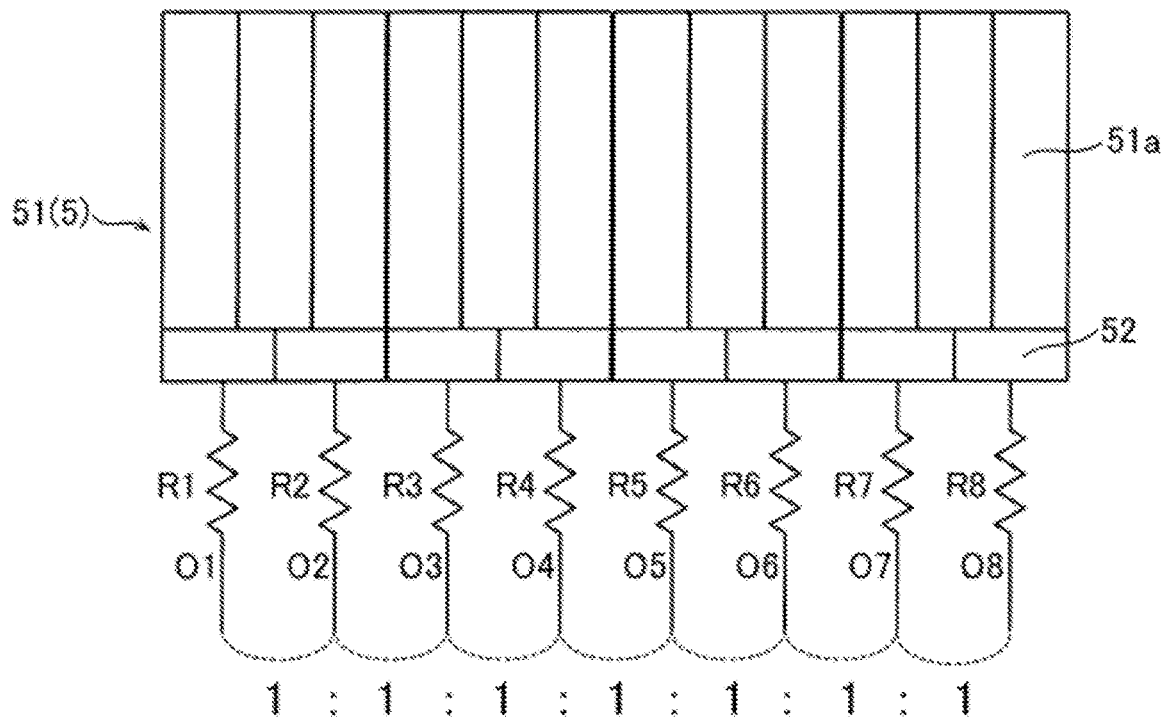

FIG. 6 is a circuit diagram in which resistors are connected to respective photodetectors arranged in a lateral direction so that weighting is equalized in a radiation detector of Comparative Example.

Figure 7:
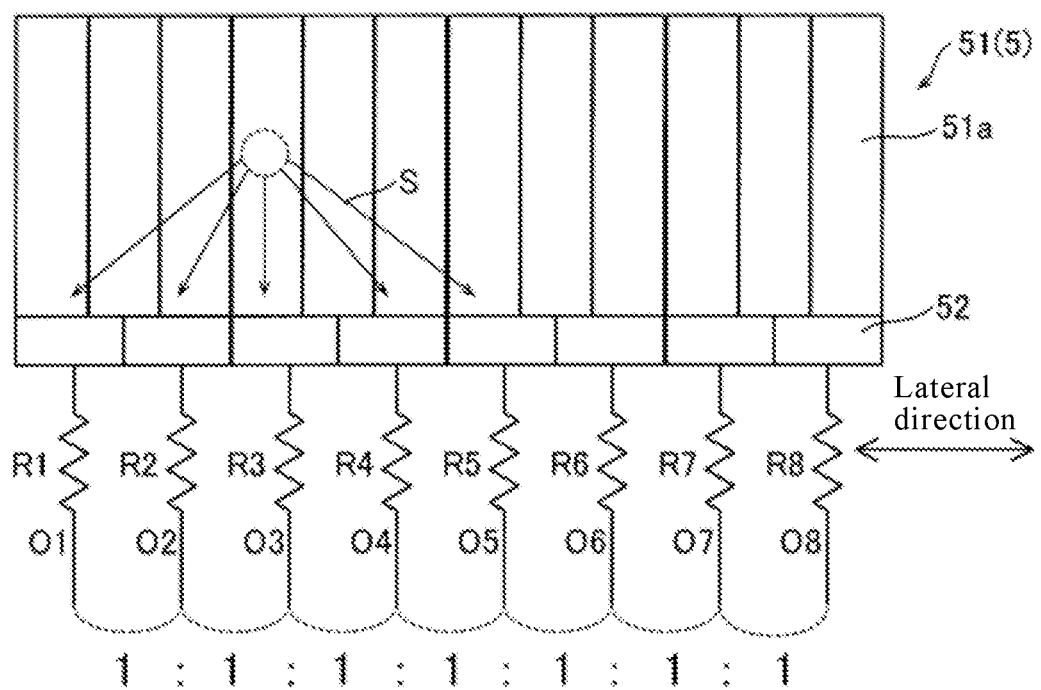

FIG. 7 is a circuit diagram schematically showing a state in which fluorescence is generated in a scintillator element arranged on the central portion side in the radiation detector of Comparative Example.

Figure 8:
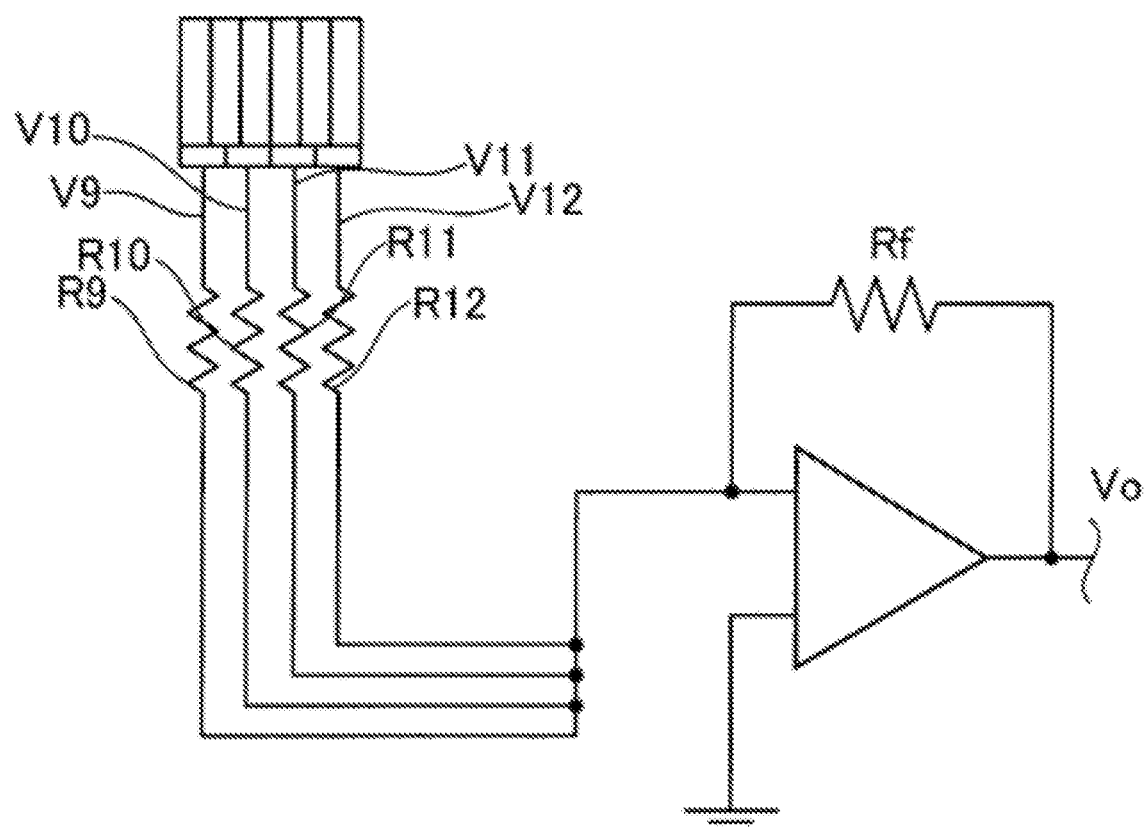

FIG. 8 is a circuit diagram schematically showing a weighting arithmetic circuit connected to photodetectors arranged in a longitudinal direction in the first embodiment of the present invention.

Figure 9:
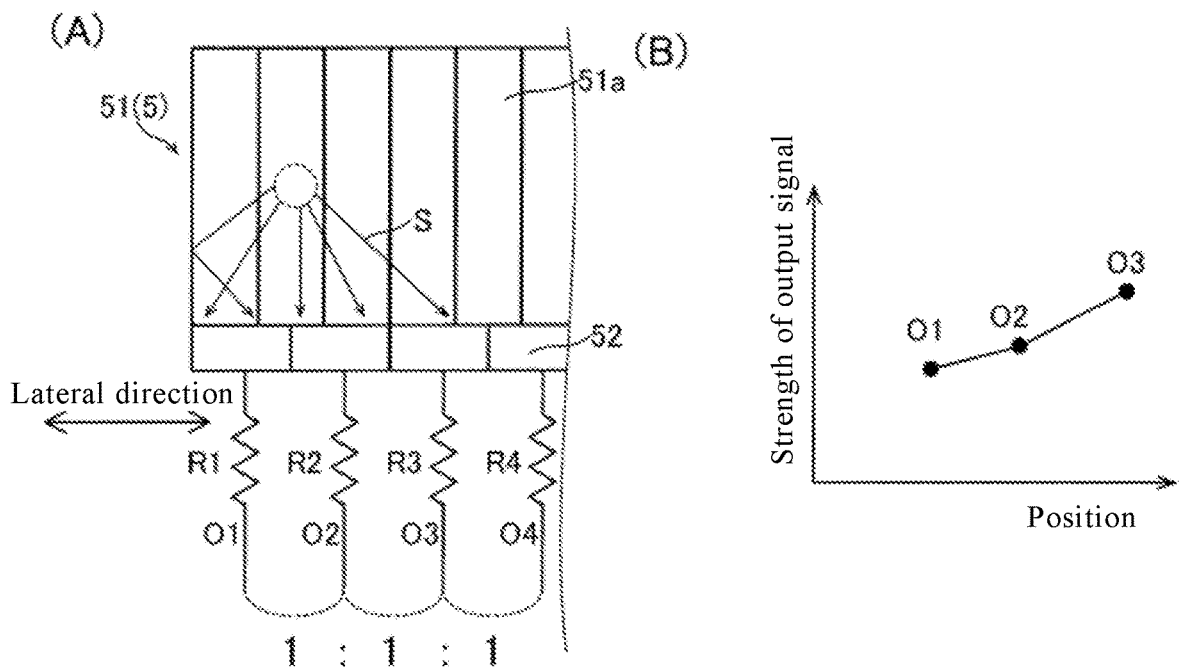

(A) of FIG. 9 is a circuit diagram schematically showing a state in which fluorescence is generated in a scintillator element at a position adjacent to the scintillator element arranged at one end portion, and (B) of FIG. 9 is a graph schematically showing a relationship between output signals and positions in cases where fluorescence is generated in the scintillator element at a position adjacent to the scintillator element arranged at one end portion.

Figure 10:
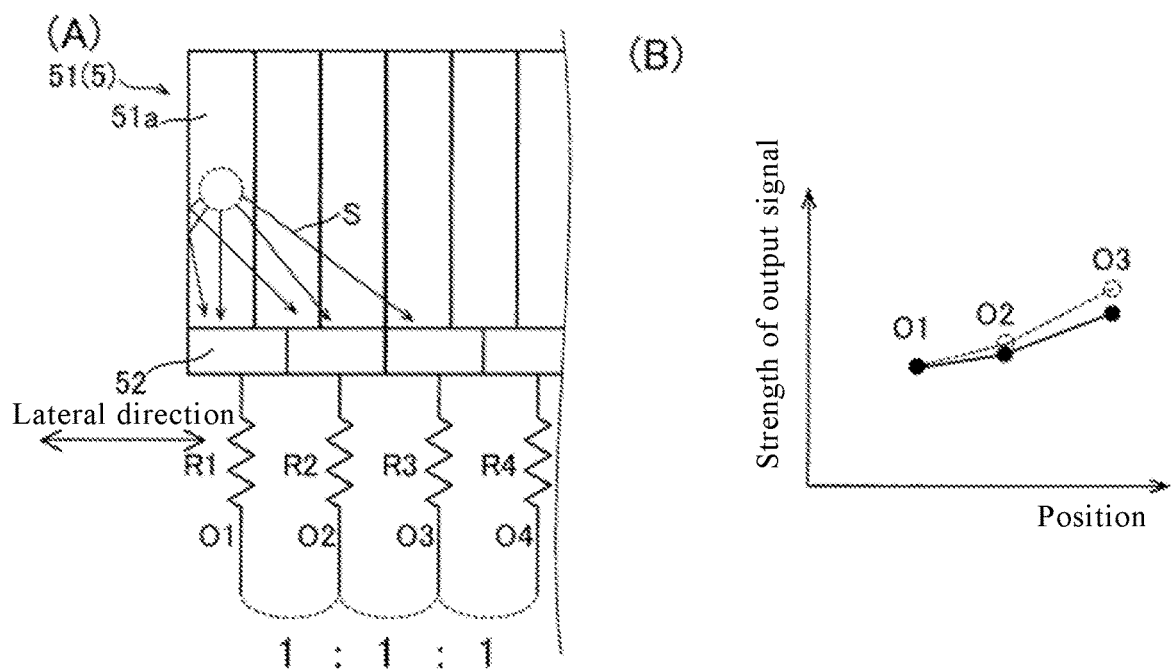

(A) FIG. 10 is a circuit diagram schematically showing a state in which fluorescence is generated in the scintillator element arranged at one end portion, and (B) of FIG. 10 is a graph schematically showing the relationship between output signals and positions in cases where fluorescence is generated in the scintillator element arranged at one end portion.

Figure 11:
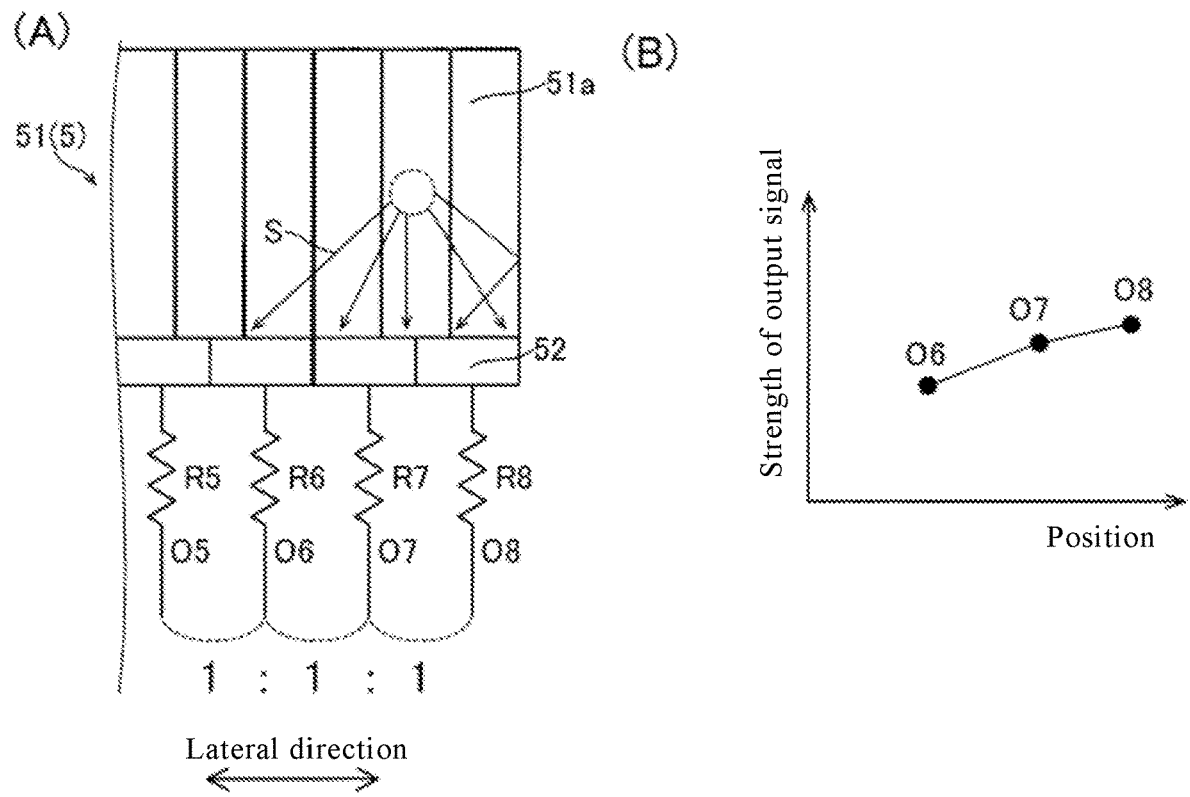

(A) of FIG. 11 is a circuit diagram schematically showing a state in which fluorescence is generated in the scintillator element at a position adjacent to the scintillator element arranged at the other end portion, and (B) of FIG. 11 is a graph schematically showing the relationship between output signals and positions in cases where fluorescence is generated in the scintillator element arranged at a position adjacent to the scintillator element arranged at the other end portion.

Figure 12:
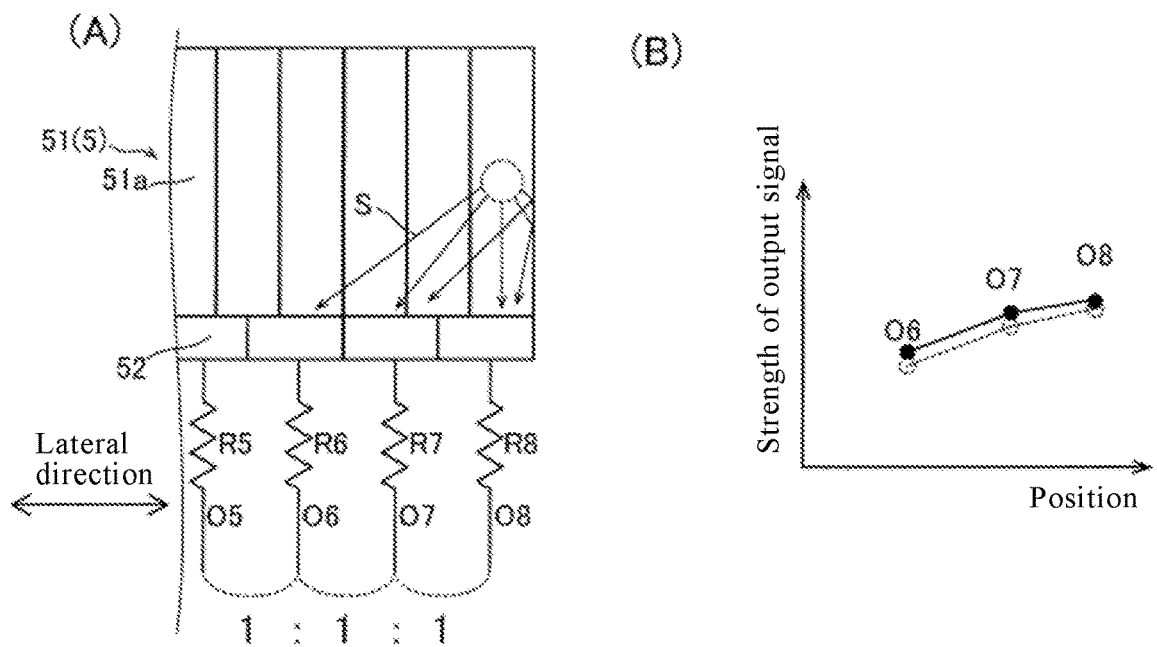

(A) of FIG. 12 is a circuit diagram schematically showing a state in which fluorescence is generated in the scintillator element arranged at the other end portion, and (B) of FIG. 12 is a graph schematically showing the relationship between output signals and positions in cases where fluorescence is generated in the scintillator element arranged at the other end portion.

Figure 13:
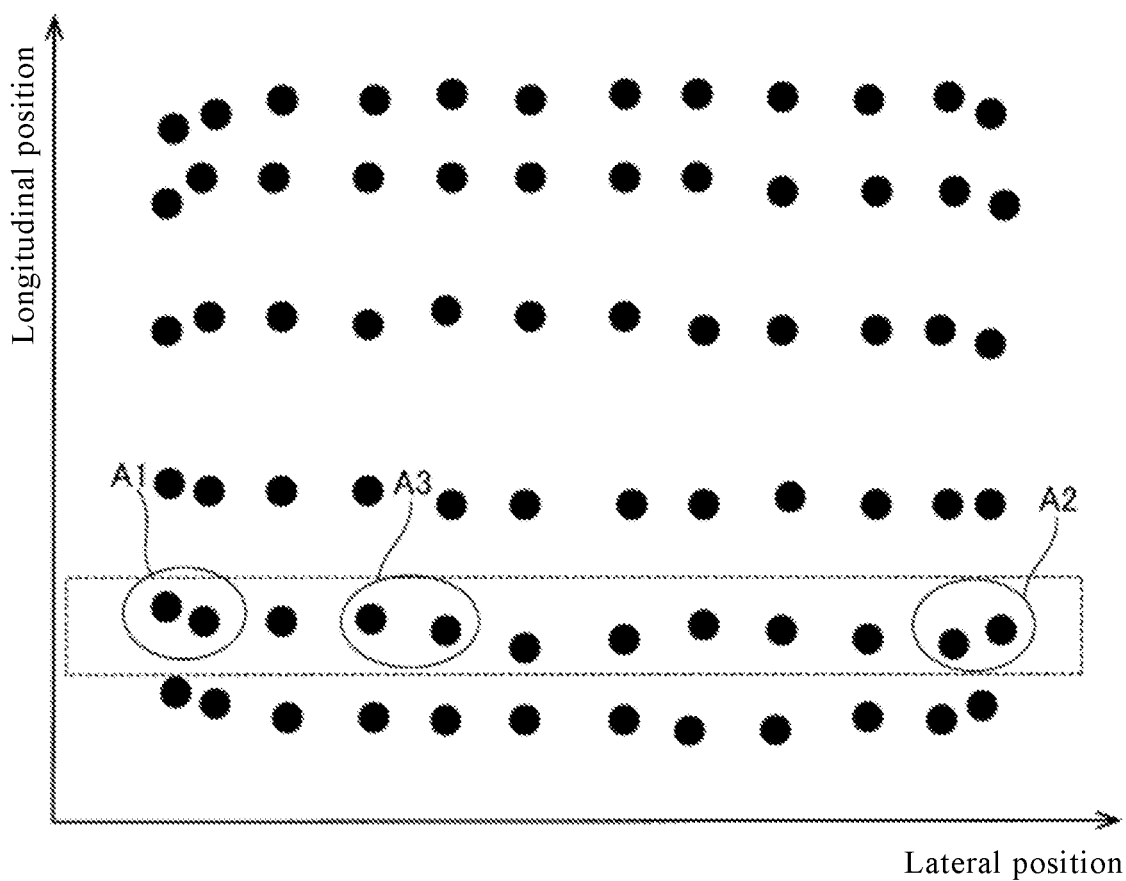

FIG. 13 is a two-dimensional map showing the positions of the specified scintillator elements in cases where radiation detectors are equally weighted in Comparative Example.

Figure 14:
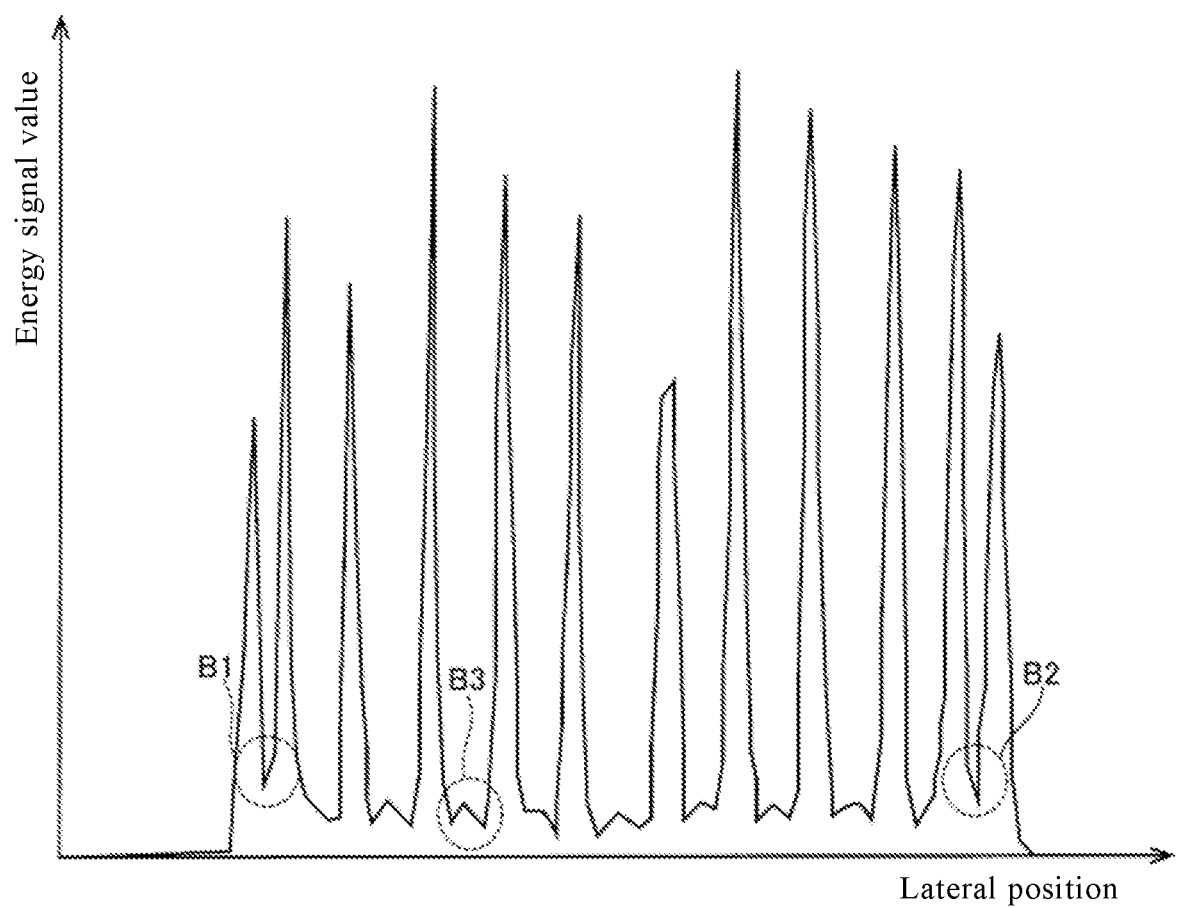

FIG. 14 is a graph showing the relationship between the positions and the energies of the specified scintillator elements in cases where radiation detectors are equally weighted in Comparative Example.

Figure 15:
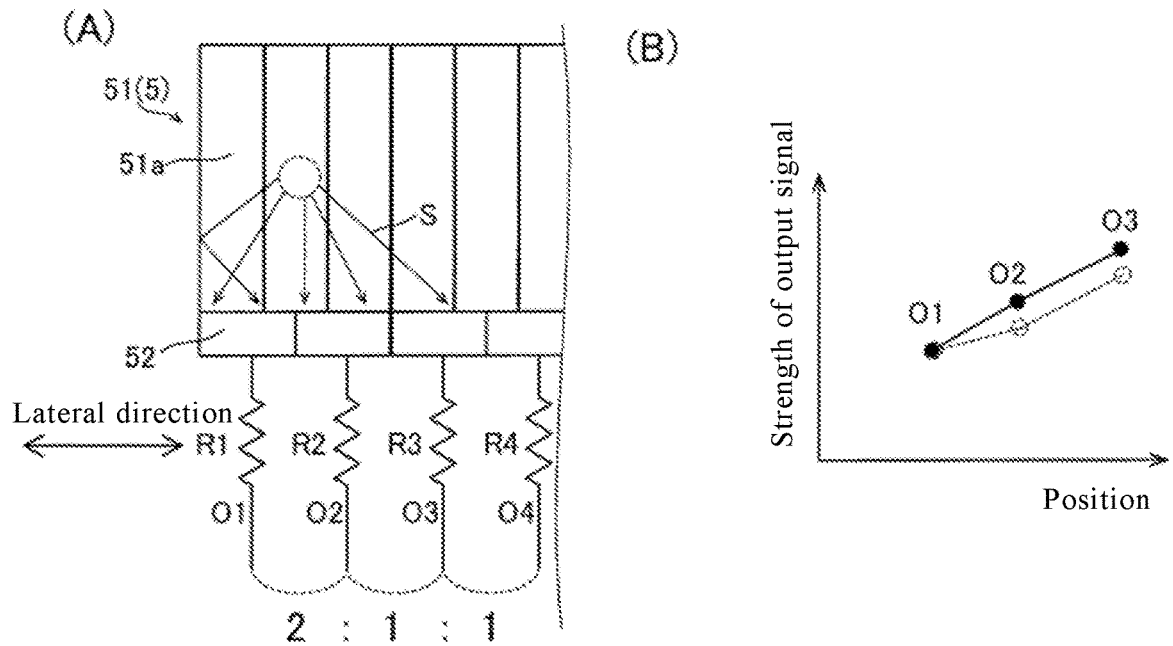

(A) of FIG. 15 is a circuit diagram schematically showing a state in which fluorescence is generated in the scintillator element arranged at a position adjacent to the scintillator arranged at one end portion, and (B) of FIG. 15 is a graph schematically showing the relationship between output signals and positions in cases where fluorescence is generated in a scintillator element arranged at a position adjacent to the scintillator arranged at one end portion.

Figure 16:
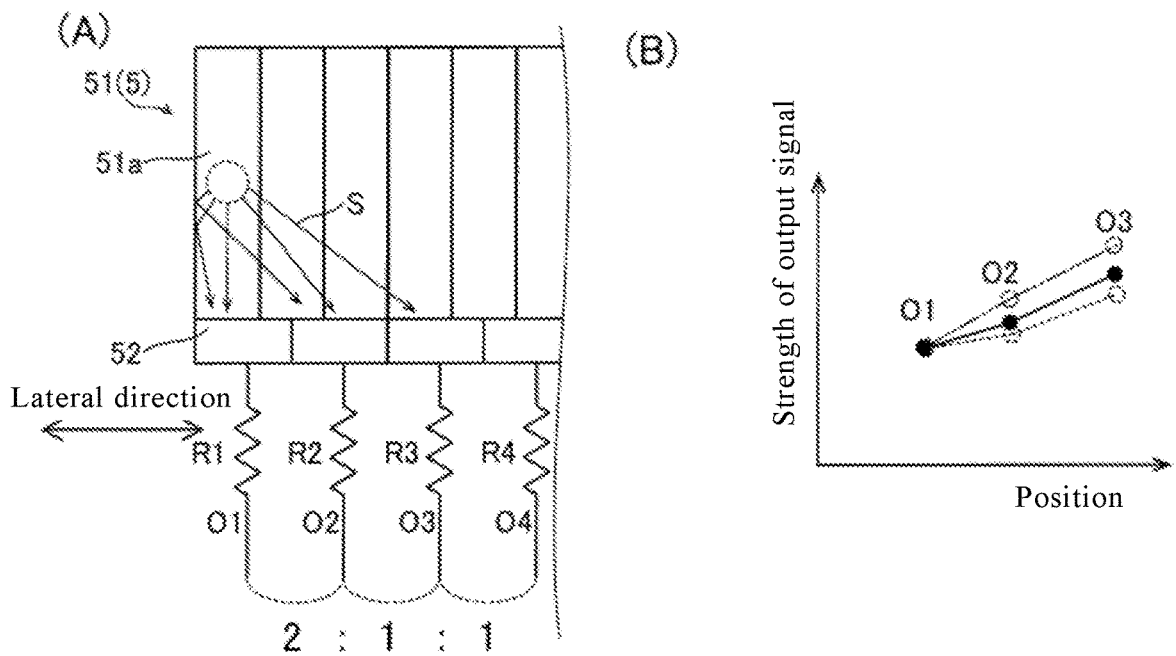

(A) of FIG. 16 is a circuit diagram schematically showing a state in which fluorescence is generated in the scintillator element arranged at one end portion, and (B) of FIG. 16 is a graph schematically showing the relationship between output signals and positions in cases where fluorescence is generated in the scintillator element arranged at one end portion.

Figure 17:
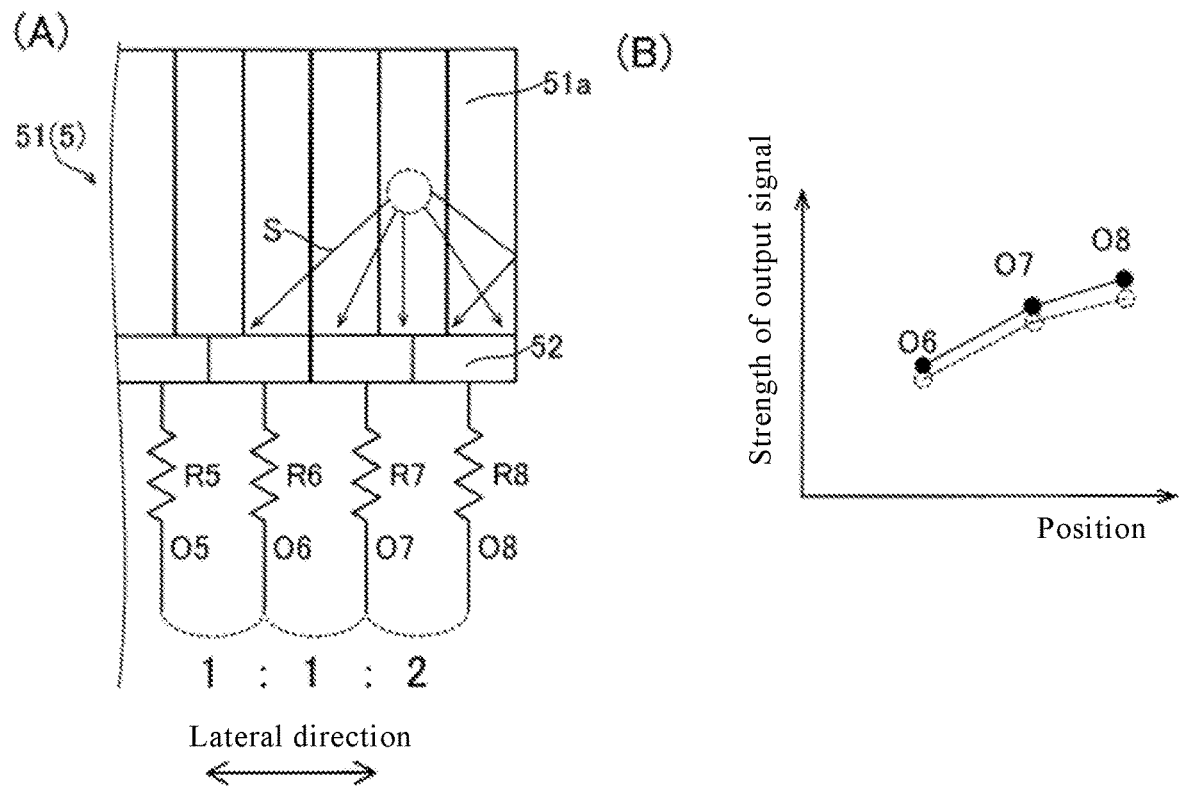

(A) of FIG. 17 is a circuit diagram schematically showing a state in which fluorescence is generated in the scintillator element arranged at a position adjacent to the scintillator arranged at the other end portion, and (B) of FIG. 17 is a graph schematically showing the relationship between output signals and positions in cases where fluorescence is generated in the scintillator element arranged at a position adjacent to the scintillator arranged at the other end portion.

Figure 18:
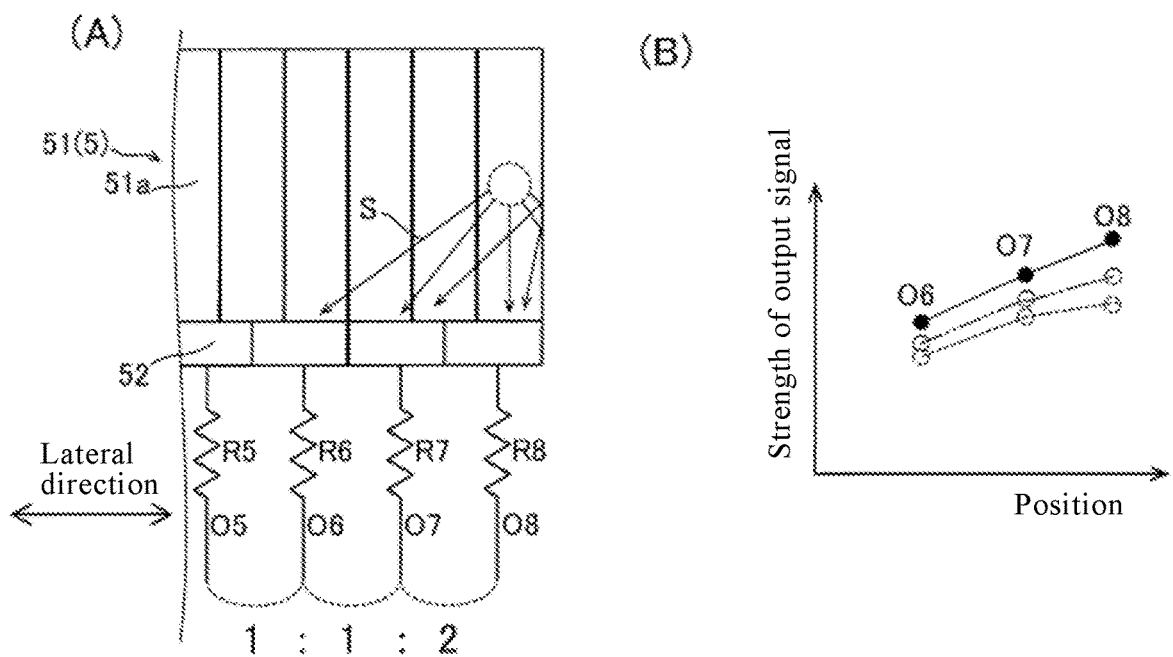

(A) of FIG. 18 is a circuit diagram schematically showing a state in which fluorescence is generated in the scintillator element arranged at the other end portion, and (B) of FIG. 18 is a graph schematically showing the relationship between output signals and positions in cases where fluorescence is generated in the scintillator element arranged the other end portion.

Figure 19:
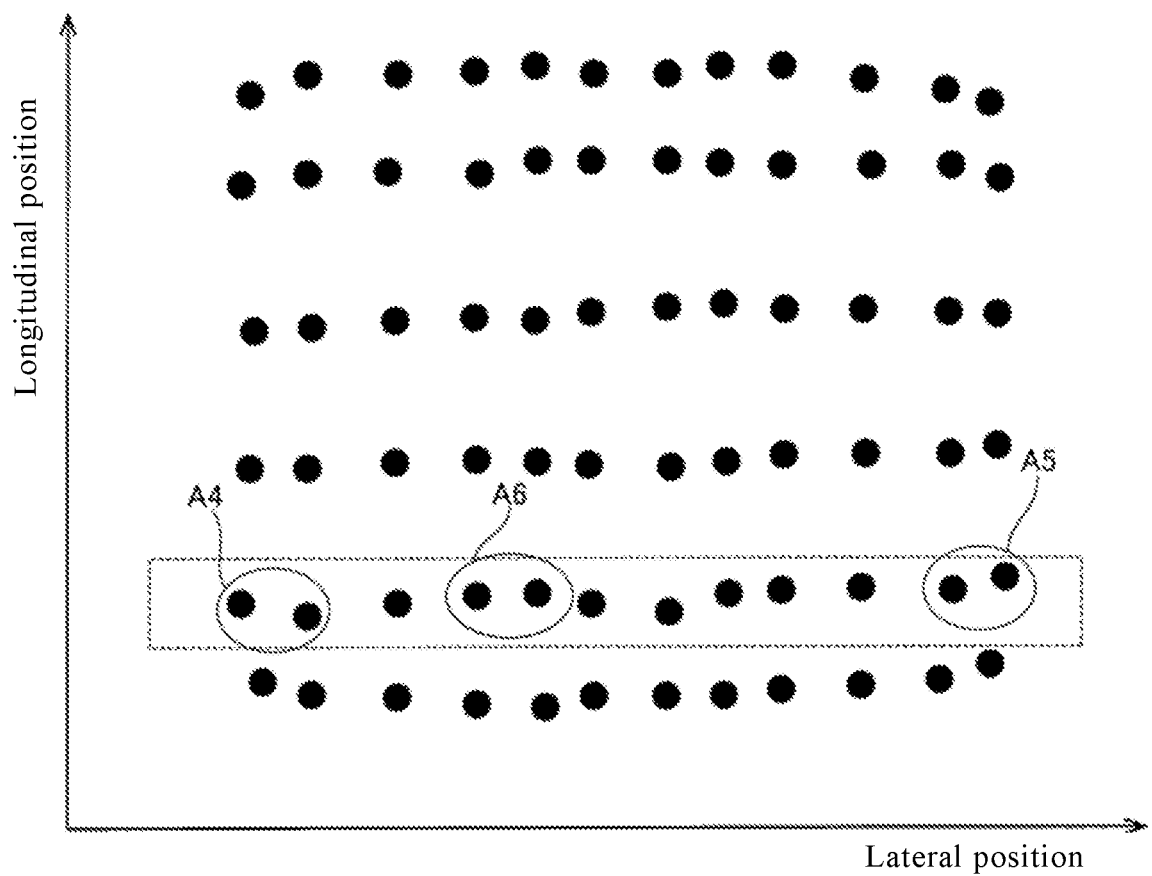

FIG. 19 is a two-dimensional map showing positions of specified scintillator elements in cases where weighting of radiation detectors is increased at the end portion according to the first embodiment of the present invention.

Figure 20:
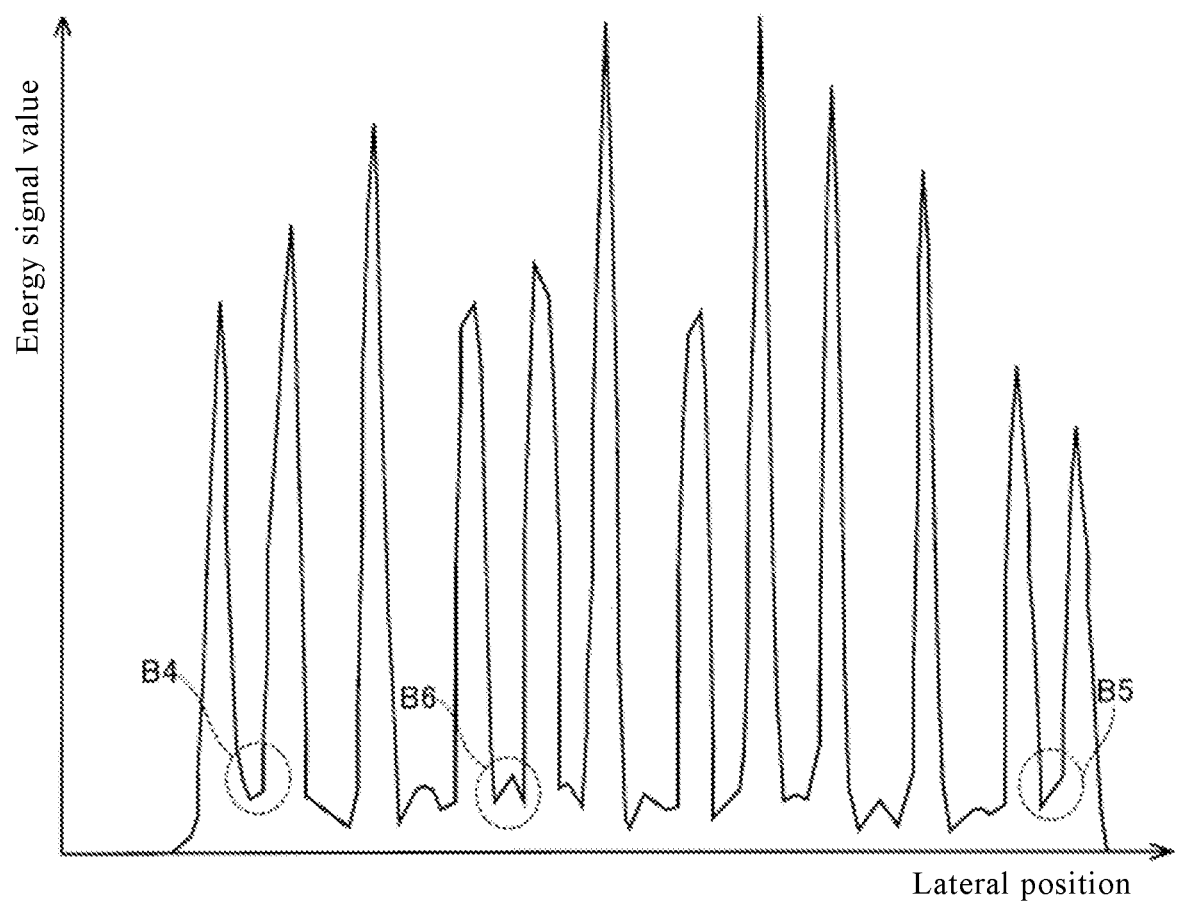

FIG. 20 is a graph showing the relationship between positions and energies of specified scintillator elements in cases where weighting of radiation detectors is increased at the end portion according to the first embodiment of the present invention.

Figure 21:
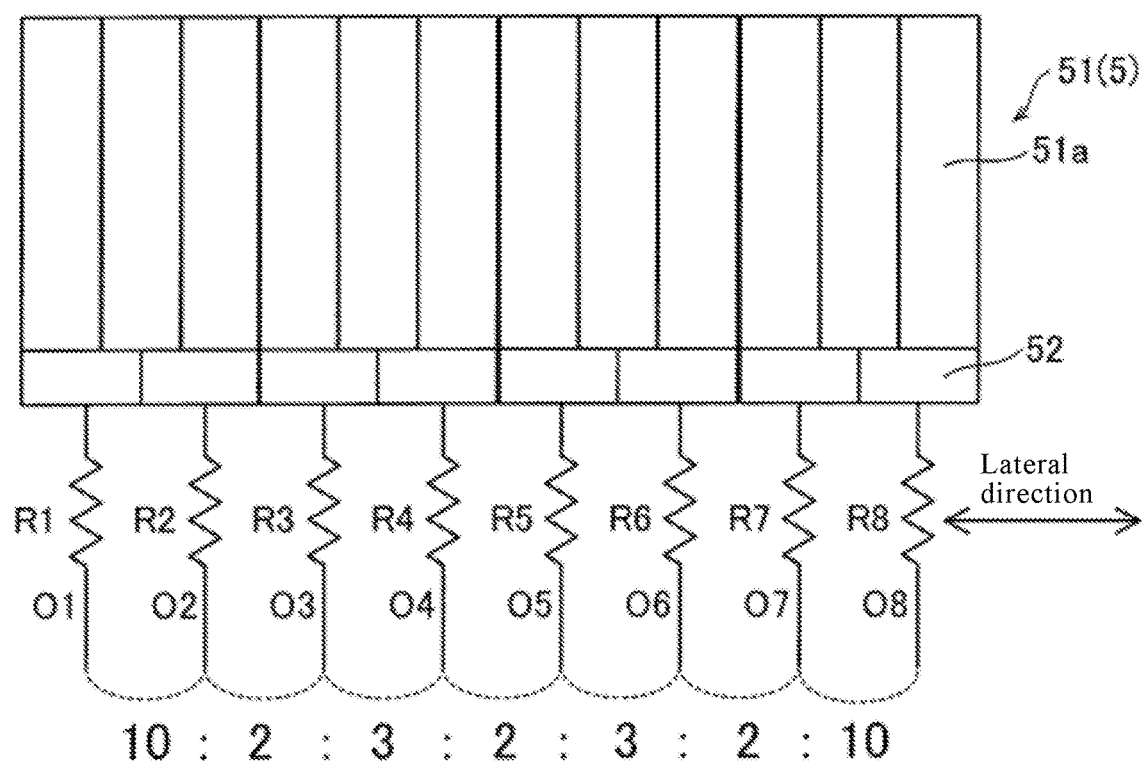

FIG. 21 is a circuit diagram in which resistors are connected to respective photodetectors arranged in the lateral direction so that weighting is changed also on the central portion side in a radiation detector according to a second embodiment of the present invention.

Figure 22:
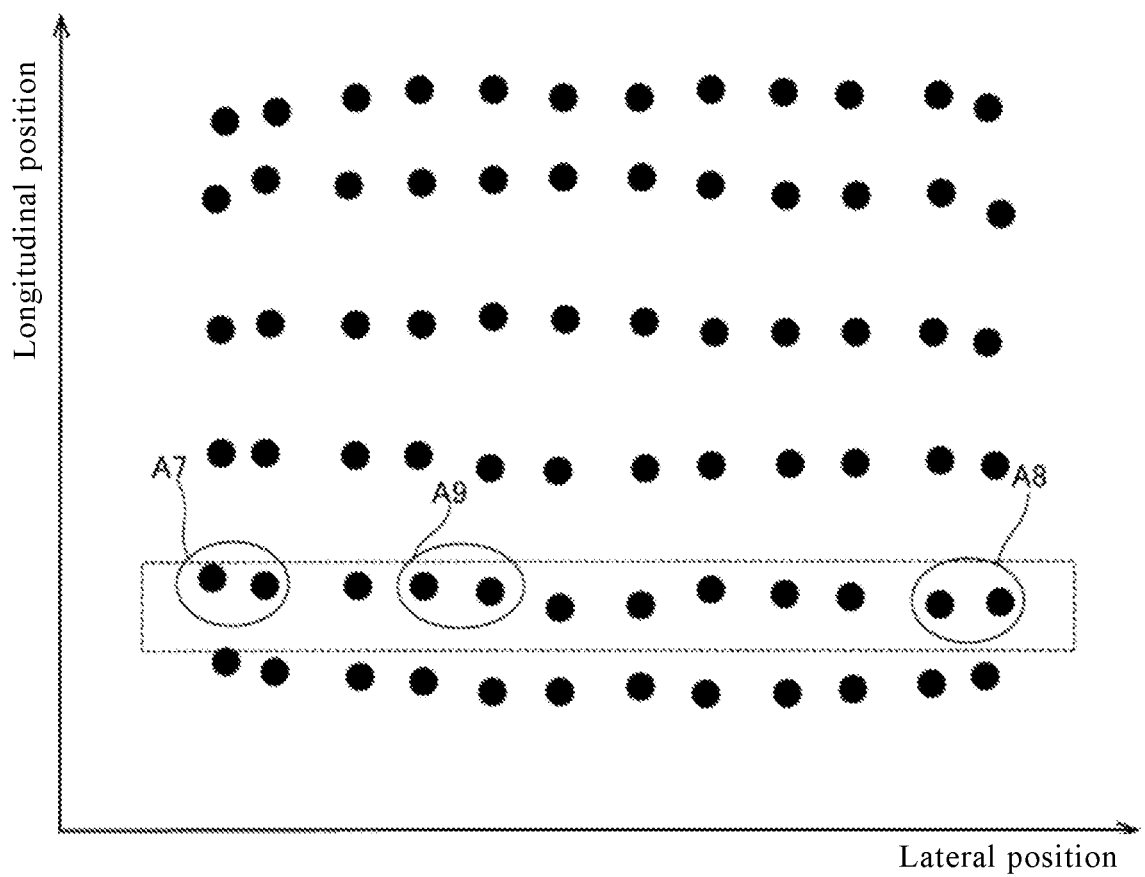

FIG. 22 is a two-dimensional map showing positions of specified scintillator elements in cases where weighting of radiation detectors is changed also on the central portion side according to the second embodiment of the present invention.

Figure 23:
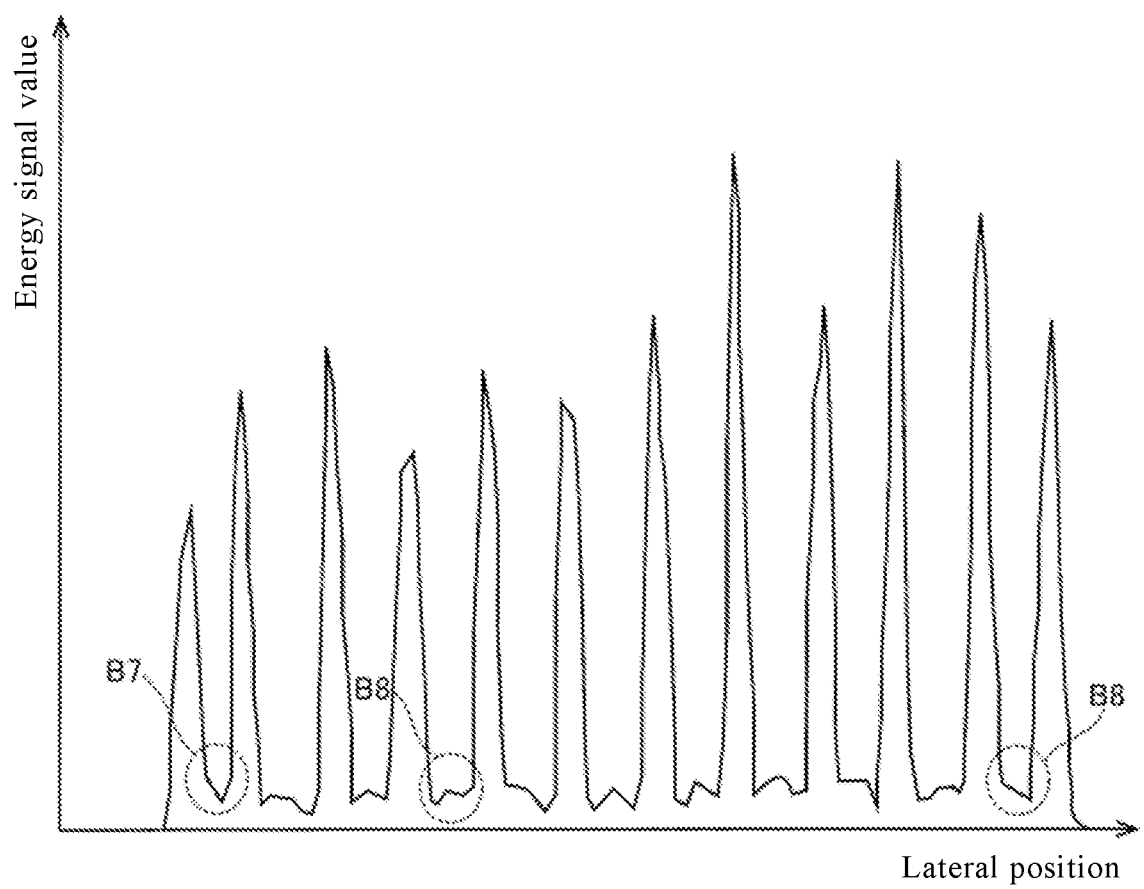

FIG. 23 is a graph showing the relationship between positions and energies of specified scintillator elements in cases where weighting of radiation detectors is changed also on the central portion side according to the second embodiment of the present invention.

Figure 24:
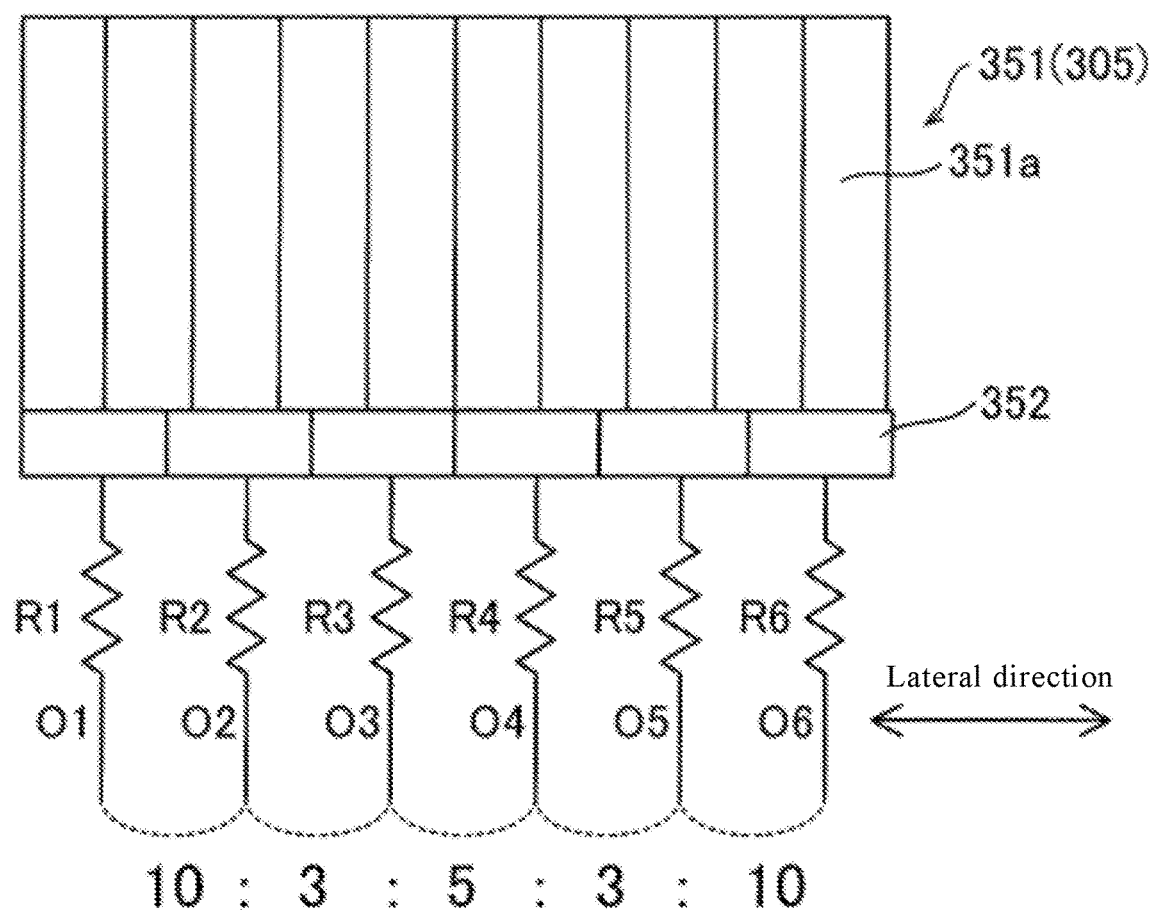

FIG. 24 is a circuit diagram in which resistors are connected respective photodetectors arranged in the lateral direction so that weighting is changed also on the central portion side in the radiation detector according to a modification of the first embodiment of the present invention.

EMBODIMENTS FOR CARRYING OUT THE INVENTION

Hereinafter, embodiments in which the present invention is embodied will be described with reference to the attached drawings.

First Embodiment

First, with reference to FIG. 1 to FIG. 20, the configuration of a PET (Positron Emission Tomography) apparatus 1 according to the first embodiment of the present invention will be described. Note that the PET apparatus 1 is an example of the "nuclear medicine diagnostic device" recited in claims.
(Configuration of PET Apparatus)

Figure 1:
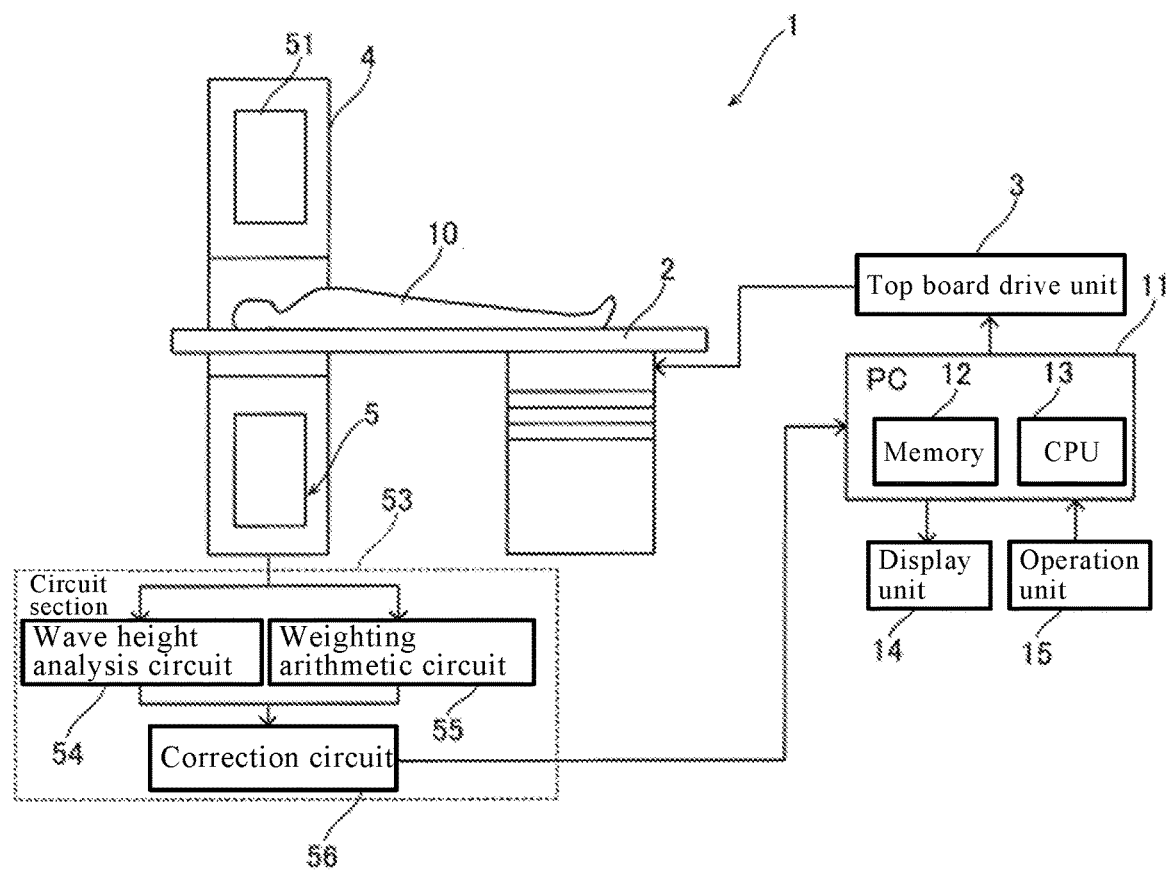
FIG. 1 is an entire configuration diagram schematically showing a configuration of a PET apparatus according to a first embodiment of the present invention.

As shown in FIG. 1, the PET apparatus 1 is configured to reconstruct an image of a subject 10 by detecting gamma rays emitted from the subject 10 and collecting the position information generated by the detected gamma rays. Specifically, the PET apparatus 1 is provided with a top board 2 for placing a subject 10 thereon, a top board drive unit 3 for moving the top board 2, a gantry 4 having an opening for introducing the subject 10 placed on the top board 2, and a radiation detector 5 arranged in the gantry 4.

Figure 2:
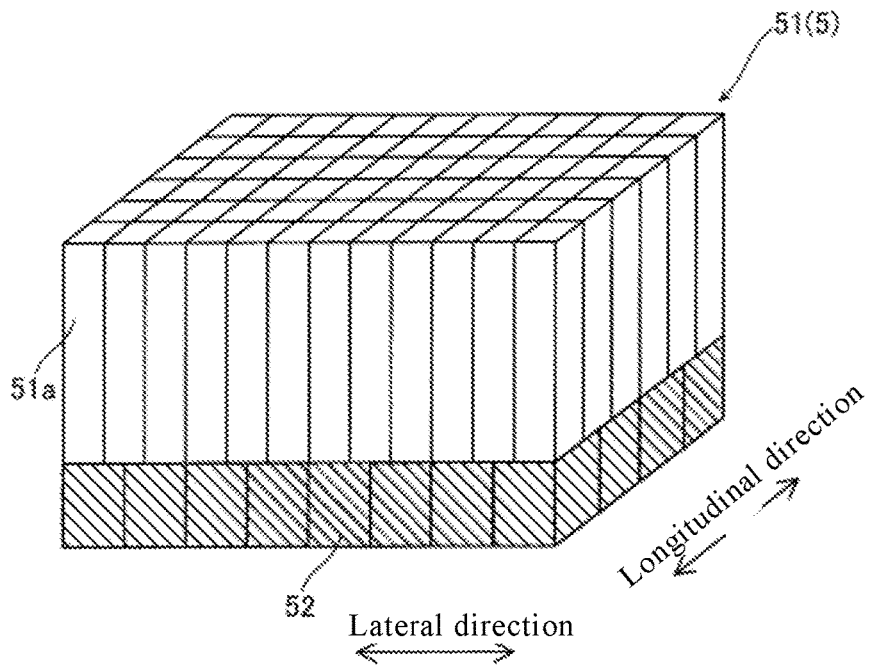
FIG. 2 is a perspective view schematically showing a scintillator and a photodetector of the PET apparatus according to the first embodiment of the present invention.

The radiation detector 5 is configured to convert gamma rays into light, further photoelectrically convert and amplify the converted light, and output as an electrical signal (detection signal). Specifically, as shown in FIG. 2, the radiation detector 5 includes a scintillator 51, a photodetector 52, and a circuit section 53 (see FIG. 1).

The scintillator 51 includes a scintillator element 51a for generating fluorescence S by absorbing gamma rays. A plurality of (12×6) scintillator elements 51a is two-dimensionally arranged. The photodetector 52 is configured to generate a photoelectron based on a trace amount of the fluorescence S generated from a plurality of scintillator elements 51a, and output an electrical signal by a photoelectron multiplier that amplifies the photoelectron. A plurality of (8×4) photodetectors 52 is two-dimensionally arranged. The plurality of scintillator elements 51a is optically connected to the plurality of respective photodetectors 52. Specifically, three pieces of scintillator elements 51a are optically connected to two pieces of photodetectors 52.

As shown in FIG. 1, the circuit section 53 includes a wave height analysis circuit 54, a weighting arithmetic circuit 55, and a correction circuit 56. The wave height analysis circuit 54 and the weighting arithmetic circuit 55 are electrically connected to the photodetectors 52 as separate circuits. The wave height analysis circuit 54 and the weighting arithmetic circuit 55 are, as separate circuits, electrically connected to the correction circuit 56.

The wave height analysis circuit 54 has a function of extracting the signal obtained by adding all outputs of the photodetectors 52 as an energy signal. The weighting arithmetic circuit 55 is configured to obtain the incidence position of gamma rays based on the detection signal output from the photodetector 52 and output it as a position signal. The correction circuit 56 has a function of correcting the outputs (position signal correction, energy-correction, and sensitivity-non-uniformity correction) of the wave height analysis circuit 54 and the weighting arithmetic circuit 55.

The PET apparatus 1 is provided with a PC (Personal Computer) 11, a display unit 14, and an operation unit 15. The PC 11 mainly includes a CPU 13 (Central Processing Unit) and a memory 12. The CPU 13 is configured to perform processing of converting the detection signal from the radiation detector 5 into a two-dimensional map and to perform processing of converting the detection signal from the radiation detector 5 into the energy spectral distribution of gamma rays. The display unit 14 is composed of an image display device, such as, e.g., a liquid crystal monitor, and performs a screen display based on the image outputs of the PC 11. The operation unit 15 is composed of a keyboard, a mouse, an operation lever, etc., for accepting operation inputs of a user. Note that the PC 11 is an example of the "controller" recited in claims.
(Weighting Arithmetic Circuit)

In the PET apparatus 1, as shown in (A) of FIG. 3, gamma rays radiated from the subject 10 are changed to fluorescence S by the scintillator element 51a. As shown in (B) of FIG. 3, the light intensity of the fluorescence S generated by the scintillator element 51a becomes the strongest at the position where the fluorescence is generated and decreases exponentially as it moves away from the position where the fluorescence is generated in the lateral direction. The photodetector 52 detects the fluorescence S generated in the scintillator element 51a, and outputs a detection signal corresponding to the intensity of the light. The PET apparatus 1 is configured to generate a position signal by adding the detection signals output by the photodetectors 52.

Here, in the PET apparatus 1, if the circuit section 53 is formed by arranging the photodetectors 52 individually for each of the plurality of scintillator elements 51a, the size of the circuit section 53 becomes enormous. Therefore, as shown in FIG. 4, by arranging a plurality of scintillator elements 51a in one photodetector 52, the circuit section 53 can be simplified. However, if a plurality of scintillator elements 51a is optically connected to one photodetector 52, it is impossible to specify (discriminate) which scintillator element 51a of the plurality of scintillator elements 51a generated the detection signal output from the photodetector 52. For this reason, in the PET apparatus 1, the weighting arithmetic circuit 55 is provided to discriminate which scintillator element 51a of the plurality of scintillator elements 51a has generated the detection signal detected in the photodetector 52. The weighting arithmetic circuit 55 is a weighting adding circuit for performing weighting on the detection signal detected by each photodetector 52 and adding the weighted detection signal. The PET apparatus 1 is configured to discriminate the position of the scintillator element 51a where fluorescence is generated based on an addition signal Vo obtained by adding the plurality of weighted detection signals by the weighting arithmetic circuit 55. Note that the weighting adding circuit is an example of the "adding circuit" recited in claims.

In the weighting arithmetic circuit 55, as shown in FIG. 4, the addition of the weighted detection signals is performed as in the following equation.

$$Vo = \sum Oi = Rf\left(\frac{V1}{R1} + \frac{V2}{R2} + \frac{V3}{R3} + \frac{V4}{R4} + \frac{V5}{R5} + \frac{V6}{R6} + \frac{V7}{R7} + \frac{V8}{R8}\right)$$

where R1, R2, R3, R4, R5, R6, R7, R8, and Rf are resistance values, and V1, V2, V3, V4, V5, V6, V7, and V8 are respective detection signals of the plurality of photodetectors 52. The output signals obtained by weighting respective detection signals of the plurality of photodetectors 52 are an output signal O1, an output signal O2, an output signal O3, an output signal O4, an output signal O5, an output signal O6, an output signal O7, and an output signal O8 in this order from one end. Rf/R1, Rf/R2, Rf/R3, Rf/R4, Rf/R5, Rf/R6, Rf/R7, and Rf/R8 are weighting factors to respective detection signals V1, V2, V3, V4, V5, V6, V7, and V8 of the plurality of photodetectors 52. Note that the weighting factor is an example of the "weighting" recited in claims. Also, note that the output signal is an example of the "signal value" recited in claims.

First, the weighting arithmetic circuit 55 of the first embodiment will be briefly described. As shown in FIG. 5, the weighting arithmetic circuit 55 is configured such that the weighting ratio at the end portion is set to be greater than that on the central portion side and the resistance value of each of the plurality of resistors R1, R2, R3, R4, R5, R6, R7, and R8 is adjusted.

Specifically, the weighting ratio is (O2−O1):(O3−O2):(O4−O3):(O5−O4):(O6−O5):(O7−O6):(O8−O7)=2:1:1:1:1:1:2 based on a reference output signal among the output signals O1, O2, O3, O4, O5, O6, O7, and O8. That is, the weighting ratio is set such that the difference between the weighting ratio at the end portion and the weighting ratio on the most end portion side among the weighting ratios on the central portion side is greater than the difference between the weighting ratios at portions other than the end portion. At this time, the weighting factor to the detection signal V1 of the photodetector 52 arranged at one end portion between the plurality of photodetectors 52 is smaller than the weighting factor to the detection signal V2 of the photodetectors 52 arranged on the central portion side between the plurality of photodetectors 52. Further, the weighting factor to the detection signal V8 of the photodetector 52 arranged at the other end portion between the plurality of photodetectors 52 is greater than the weighting factor to the detection signal V7 of the photodetector 52 arranged on the central portion side between the plurality of photodetectors 52. The weighting ratio described above can be determined based on simulations.

Here, the calculation of the resistance value will be exemplified below using specific numerical values. When the reference output signal is O1 and R1=600 [Ω] as examples, the resistance values of the plurality of resistors R1, R2, R3, R4, R5, R6, R7, and R8 are R2=200 [Ω], R3=150 [Ω], R4=120 [Ω], R5=100 [Ω], R6=85 [Ω], R7=75 [Ω], and R8=60 [Ω], respectively. That is, based on the weighting ratio, since O2−O1=2×O1, O2 is 3×O1. Here, to double the output signal O2 against the output signal O1, the resistance value of the resistor R2 is set to ⅓ of the resistance value of the resistor R1. Therefore, R2 becomes 200 [Ω] (R2=200 [Ω]). The resistor R3, resistor R4, resistor R5, resistor R6, resistor R7, and resistor R8 are calculated in the same manner. Next, the weighting arithmetic circuit 55 of Comparative Example will be described.

<Weighting Arithmetic Circuit of Comparative Example>

In the weighting arithmetic circuit 55 of Comparative Example, as shown in FIG. 6, the plurality of resistors R1, R2, R3, R4, R5, R6, R7, and R8 electrically connected to the plurality of photodetectors 52 are adjusted so that the weighting ratio based on the differences between the plurality of weighted output signals O1, O2, O3, O4, O5, O6, O7, and O8 becomes equal. That is, the weighting ratio is (O2−O1):(O3−O2):(O4−O3):(O5−O4):(O6−O5):(O7−O6):(O2−O1)=1:1:1:1:1:1:1 based on a reference output signal set from between output signals O1, O2, O3, O4, O5, O6, O7, and O8.

Here, the calculations of the resistance values are exemplified below using specific numerical values. When the reference output signal is O1 and R1=600 [Ω], the resistance values of the plurality of resistors R1, R2, R3, R4, R5, R6, R7, and R8 are R2=300 [Ω], R3=200 [Ω], R4=150 [Ω], R5=120 [Ω], R6=100 [Ω], R7=85 [Ω], and R8=75 [Ω], as examples. That is, based on the weighting ratio, since O2−O1 is O1, O2 is 2×O1. To double the output signal O2 against the output signal O1, the resistance value of the resistor R2 is set to be one-half (½) of the resistance value of the resistor R1. Therefore, R2=300 [Ω]. The resistor R3, resistor R4, resistor R5, resistor R6, resistor R7, and resistor R8 are calculated in the same manner.

With this, since the resistance values of the plurality of resistors R1, R2, R3, R4, R5, R6, R7, and R8 are adjusted so that the weighting ratio of the differences between the output signals O1, O2, O3, O4, O5, O6, O7, and O8 becomes equal, as shown in FIG. 7, the output signals O1, O2, O3, O4, and O5 corresponding to the positions of the photodetectors 52 are obtained in cases where fluorescence S is sufficiently diffused.

The aforementioned weighting arithmetic circuit 55 is electrically connected to the plurality of photodetectors 52 arranged in one direction (lateral direction) of the two-dimensionally arranged scintillator elements 51a. With this, the lateral position of the scintillator element 51a where the fluorescence S is generated is discriminated. As shown in FIG. 8, the weighting arithmetic circuit 55 is electrically connected to a plurality of photodetectors 52 arranged in the other direction (longitudinal direction) of the two-dimensionally arranged scintillator elements 51a. With this, the longitudinal position of the scintillator element 51a where fluorescence S is generated is discriminated. With these results, the two-dimensional position of the scintillator element 51a where fluorescence S is generated can be discriminated using the plurality of photodetectors 52.

Here, in cases where fluorescence S is emitted in the scintillator element 51a arranged adjacent to the scintillator element 51a arranged at one end portion of the plurality of scintillator elements 51a shown in (A) of FIG. 9, since the fluorescence S is reflected in the scintillator element 51a arranged at one end portion, the fluorescence S will not be sufficiently diffused. Similarly, also in cases where fluorescence S is emitted in the scintillator element 51a arranged at one end portion of the plurality of scintillator elements 51a shown in (A) of FIG. 10, fluorescence S will not be sufficiently diffused. In these cases, as shown in (B) of FIG. 9 and (B) of FIG. 10, the plurality of output signals O1, O2, and O3 corresponding to the positions of the photodetectors 52 are close to each other. Note that in (B) of FIG. 10, the result of (B) of FIG. 9 is indicated by a dotted line. Therefore, the addition signal Vo obtained by adding the plurality of output signals O1, O2, and O3 is also close to each other.

Here, in cases where fluorescence S is emitted in the scintillator element 51a adjacent to the scintillator element 51a arranged at the other end portion of the plurality of scintillator elements 51a shown in (A) of FIG. 11, the fluorescence S will not be sufficiently diffused. Similarly, also in cases where fluorescence S is emitted in the scintillator element 51a arranged at the other end portion of the plurality of scintillator elements 51a shown in (A) of FIG. 12, fluorescence S will not be sufficiently diffused. In these cases, as shown in (B) of FIG. 11 and (B) of FIG. 12, the plurality of output signals O6, O7, and O8 corresponding to the positions of the photodetectors 52 are close to each other. Note that in (B) of FIG. 12, the result of (B) of FIG. 11 is indicated by a dotted line. Therefore, the addition signal Vo obtained by adding the plurality of output signals O6, O7, and O8 is also close.

Based on the weighting ratio of such Comparative Example, a map (two-dimensional map) showing a two-dimensional array of scintillator elements 51a is formed based on the addition signal Vo of the plurality of output signals O1, O2, O3, O4, O5, O6, O7, and O8. As shown in FIG. 13, on the two-dimensional map, the interval between the point showing the scintillator element 51a arranged at the end portion and the point showing the scintillator element 51a adjacent to the scintillator element 51a arranged at the end portion in the region surrounded by A1, A2, and A3 is closer than the interval between the other scintillator elements 51a. As a result, the map discriminating ability is decreased.

Further, based on the weighting ratio of such Comparative Example, a graph showing the relationship between the lateral position of the scintillator element 51a and the peak value of the energy signal value measured by the wave height analysis circuit 54 is formed based on the addition signal Vo of the plurality of output signals O1, O2, O3, O4, O5, O6, O7, and O8. As shown in FIG. 14, on the graph, the interval of the valley portions between the peak value at the end portion and the peak value adjacent to the peak value at the end portion is smaller than the interval between the peak values at the central portion, in the region surrounded by B1, B2, and B3.

As described above, in the weighting arithmetic circuit 55 of Comparative Example, in cases where fluorescence S is generated in the scintillator element 51a arranged at the end portion, the calculation accuracy of the weighting arithmetic circuit 55 is decreased, so that the discrimination accuracy is decreased, as compared with the case in which fluorescence S is generated in the scintillator element 51a arranged on the central portion side. That is, in the weighting arithmetic circuit 55 of Comparative Example, there is a positional dependency that the accuracy of discrimination changes depending on the respective positions of the plurality of scintillator elements 51a.

Next, the weighting arithmetic circuit 55 of the first embodiment will be described in detail.

<Weighting Arithmetic Circuit of First Embodiment>

The weighting arithmetic circuit 55 of the first embodiment is configured to suppress the positional dependency by adjusting the weighting ratio to adjust the respective resistance values of the plurality of resistors R1, R2, R3, R4, R5, R6, R7, and R8.

Specifically, as described above, the weighting ratio is set to (O2−O1):(O3−O2):(O4−O3):(O5−O4):(O6−O5):(O7−O6):(O8−O7)=2:1:1:1:1:1:2.

As shown in (A) of FIG. 15, in cases where fluorescence S is emitted in the scintillator element 51a at the position adjacent to the scintillator element 51a arranged at one end side portion between the plurality of scintillator elements 51a, as shown in (B) of FIG. 15, the results of the output signals O1, O2, and O3 of the first embodiment are shown by a solid line, and the results of O1, O2, and O3 of Comparative Example are shown a broken line. The output signal O2 becomes greater than the output signal O2 of Comparative Example (see (B) of FIG. 9) because the resistance value of the resistor R2 is reduced (300 [Ω] to 200 [Ω]) due to the fact that the weighting ratio corresponding to (O2−O1) became twice the weighting ratio in Comparative Example (see (A) of FIG. 9). The difference between the output signal O2 and the output signal O1 became greater than the difference in Comparative Example (see (B) of FIG. 10) due to the fact that the weighting ratio corresponding to (O2−O1) became twice the weighting ratio of Comparative Example (see (A) of FIG. 9). Further, the output signal O3 became greater than the output signal O3 of Comparative Example (see (B) of FIG. 9) because the resistance value of the resistor R3 became smaller (200 [Ω] to 150 [Ω]) due to the fact that the weighting ratio corresponding to (O2−O1) became twice the weighting ratio of Comparative Example (see (A) of FIG. 9). The difference between the output signal O3 and the output signal O2 becomes close to the difference in Comparative Example (see (B) of FIG. 10) because both the output signal O3 and the output signal O2 became large.

As shown in (A) of FIG. 16, in cases where fluorescence S is emitted in the scintillator element 51a at the position of the one end side of the plurality of scintillator elements 51a, as shown in (B) of FIG. 16, the result of the output signals O1, O2, and O3 of the first embodiment are shown by a solid line, and the result of the output signals O1, O2, and O3 of Comparative Example (see (B) of FIG. 10) is shown a broken line. In this case, the differences between the output signals O1, O2, O3 of the first embodiment and the output signals O1, O2, and O3 of Comparative Example become the same result as in the case of FIG. 15.

In (B) of FIG. 16, the graph ((B) of FIG. 15) in cases where fluorescence S is emitted in the scintillator element 51a at a position adjacent to the scintillator arranged at one end portion side between the plurality of scintillator elements 51a is shown by a two-dot chain line. The difference between the output signals O2 became greater than the difference between the output signals O2 of Comparative Example (see (B) of FIG. 10) because the weighting ratio corresponding to (O2−O1) in the weighting ratio became twice the weighting ratio of Comparative Example. Further, the difference between the output signals O3 becomes close to the difference between the output signals O3 of Comparative Example (see (B) of FIG. 10). Therefore, the difference between the addition signal Vo in cases where fluorescence S is emitted in the scintillator element 51*a* at the position adjacent to the scintillator arranged at one end portion side and the addition signal Vo in cases where fluorescence S is emitted in the scintillator element 51*a* at the position of the one end portion side becomes greater than the difference of addition signals Vo of Comparative Example.

As shown in (A) of FIG. 17, in cases where fluorescence S is emitted in the scintillator element 51*a* at the position adjacent to the scintillator arranged at the other end portion side between the plurality of scintillator elements 51*a*, the results of the output signals O6, O7, and O8 of the first embodiment are shown by a solid line, and the results of the output signals O6, O7, and O8 of Comparative Example (see (B) of FIG. 11) are shown by a broken line, as shown in (B) of FIG. 17. The output signal O8 becomes greater than the output signal O8 of Comparative Example (see (B) of FIG. 11) because the resistance value of the resistor R8 is reduced (75 [Ω] to 60 [Ω]) due to the fact that the weighting ratio corresponding to (O8–O7) became twice the weighting ratio of Comparative Example (see (A) of FIG. 11). The difference between the output signal O8 and the output signal O7 became greater than the difference in Comparative Example (see (B) of FIG. 11) because the weighting ratio corresponding to (O8–O7) became twice the weighting ratio of Comparative Example (see (A) of FIG. 11). Further, the output signal O7 became greater than the output signal O7 of Comparative Example (see (B) of FIG. 11) because the resistance value of the resistor R7 became smaller (85 [Ω] to 75 [Ω]) due to the fact that the weighting ratio corresponding to (O2–O1) became twice the weighting ratio of Comparative Example (see (A) of FIG. 11). The difference between the output signal O7 and the output signal O6 becomes close to the difference in Comparative Example (see (B) of FIG. 11) because both the output signal O7 and the output signal O6 become large.

As shown in (A) of FIG. 18, in cases where fluorescence S is emitted in the scintillator element 51*a* at the position at the end portion between the plurality of scintillator elements 51*a*, as shown in (B) of FIG. 18, the results of the output signals O6, O7, and O8 of first embodiment are shown by a solid line, and the results of the output signal O6, O7, and O8 of Comparative Example (see (B) of FIG. 12) are shown by a broken line. In this case, the differences between the output signals O6, O7, and O8 of the first embodiment and the output signals O6, O7, and O8 of Comparative Example become the same result, respectively, as in the case of FIG. 17.

In (B) of FIG. 18, a graph ((B) of FIG. 17) in cases where fluorescence S is emitted in the scintillator element 51*a* at a position adjacent to the end portion between the plurality of scintillator elements 51*a* is shown by a two-dot chain line. The difference between the output signals O8 became greater than the difference between the output signals O8 of Comparative Example (see (B) of FIG. 12) because the weighting ratio corresponding to (O8–O7) in the weighting ratio became twice the weighting ratio of Comparative Example. Further, the difference between the output signals O7 becomes close to the difference between the output signals O7 of Comparative example (see (B) of FIG. 12). Therefore, the difference between addition signal Vo in cases where fluorescence S is emitted in the scintillator element 51*a* at the position adjacent to the end portion and the addition signal Vo in cases where fluorescence S is emitted in the scintillator element 51*a* at the position of the end portion becomes greater than the difference of the addition signals Vo of Comparative Example.

Here, as shown in FIG. 19, based on the addition signal Vo of the plurality of output signals O1, O2, O3, O4, O5, O6, O7, and O8, a two-dimensional map showing the two-dimensional arrangement of the scintillator elements 51*a* is formed. On the two-dimensional map, the interval between the point showing the scintillator element 51*a* arranged at the end portion and the point showing the scintillator element 51*a* adjacent to the scintillator element 51*a* arranged at the end portion in the regions surrounded by A4, A5, and A6 is greater than the interval in Comparative Example. Further, as shown in FIG. 20, based on the addition signal Vo of the plurality of output signals O1, O2, O3, O4, O5, O6, O7, and O8, a graph showing the relationship between the lateral positions of the scintillator elements 51*a* and the peak values of the energy signal values. On the graph, the interval between the valley portions of the peak value at the end portion and the peak value at the portion adjacent to the end portion in the regions surrounded by B4, B5, and B6 is greater than the interval in Comparative Example.

In this manner, in the weighting arithmetic circuit 55, by adjusting the weighting ratio and adjusting the plurality of resistors, it is possible to suppress the deterioration of the calculation accuracy of the weighting arithmetic circuit 55 at the end portions (i.e., both the end portions in the lateral direction).

(Effects of First Embodiment)

In this first embodiment, the following effects can be obtained.

In the first embodiment, as described above, a plurality of photodetectors 52 for detecting fluorescence S generated in the scintillator element 51*a* and a PC 11 for distinguishing the generation position of the fluorescence S based on the signals O1, O2, O3, O4, O5, O6, O7, and O8 that has weighted respective detection signals V1, V2, V3, V4, V5, V6, V7, and V8 of the plurality of photodetectors 52 are provided. The weighting of the detection signal V1 of the photodetector 52 arranged on the end portion side is set to be greater than the weighting of the detection signal V2 of the photodetector 52 arranged on the central portion side. As a result, it becomes possible to easily discriminate between the case in which fluorescence S is generated in the scintillator element 51*a* arranged on the end portion side and the case in which fluorescence S is generated in the scintillator element 51*a* arranged on the central portion side because the difference between the weighted detection signal V1 of the photodetector 52 arranged on the end portion side and the weighted detection signal V2 of the photodetector 52 arranged on the central portion side becomes greater than the difference between those of the photodetectors 52 arranged on the central portion side. As a result, it is possible to easily perform the adjustment for differentiating the respective strengths of the detection signals V1 and V8 of the photodetectors 52 arranged at the end portions and the respective strengths of the detection signals V2 and V7 of the photodetectors 52 adjacent to the photodetectors 52 arranged at the end portions, without requiring labor such as an adjustment of the optical partition wall or the light guide to accurately specify the scintillator element 51*a* in which the fluorescence S is generated. Also, it is possible to suppress the structure of the radiation detector 5 from being complicated because it is possible to differentiate the respective strengths of the detection signals V1 and V8 of the photodetectors 52 arranged at the end portions and the respective strengths of the detection signals V2 and V7 of the photodetectors 52 adjacent to the photodetectors 52 arranged at the end portions even if no optical partition or a light guide is used. Further, the position of the fluorescence S generated in the scintillator element 51a arranged on the end portion side can be accurately discriminated.

Also, in the first embodiment, as described above, the weighting factor is based on the weighting ratio. The weighting ratio is set so that the weighting ratio on the end portion side is greater than that of the weighting ratio on the central portion side. This makes it possible to increase the difference between the respective output signals O1 and O8 of the photodetectors 52 arranged on the end portions and the respective output signals O2 and O7 of the photodetectors 52 adjacent to the photodetectors 52 arranged on the end portions, as compared with the difference between the output signals O2, O3, O4, O5, O6, and O7 of the photodetectors 52 arranged on the central portion side. As a result, it is possible to easily discriminate the position of the scintillator element 51a in cases where fluorescence S is generated in the scintillator element 51a arranged on the end portion, as compared with the case in which the weighting ratio is set equally.

Further, in the first embodiment, as described above, the difference between the weighting ratio at the end portion and the weighting ratio of the most end portion side among the weighting ratios on the central portion side is set to be greater than the difference between the weighting ratios other than those at the end portions. This makes it possible to increase the difference between the respective output signals O1 and O8 of the photodetectors 52 arranged at the end portions and the respective output signals O2 and O7 of the photodetectors 52 adjacent to the photodetectors 52 arranged at the end portion, as compared with the difference between the output signals O2, O3, O4, O5, O6, and O7 of the photodetectors 52 arranged on the central portion side. As a result, the position of the scintillator element 51a can be more easily discriminated in cases where fluorescence S is generated in the scintillator element 51a arranged at the end portion, as compared with the case in which the weighting ratio is set equally.

In the first embodiment, as described above, the radiation detector 5 is further provided with the plurality of resistors R1, R2, R3, R4, R5, R6, R7, and R8 for weighting the respective detection signals V1, V2, V3, V4, V5, V6, V7, and V8 output from the plurality of photodetectors 52. The respective resistance values of the plurality of resistors R1, R2, R3, R4, R5, R6, R7, and R8 are adjusted based on the weighting ratio. This makes it possible to easily weight the respective detection signals V1, V2, V3, V4, V5, V6, V7, and V8 of the plurality of photodetectors 52.

Also in the first embodiment, as described above, the radiation detector 5 is further provided with the weighting arithmetic circuit 55 that adds the output signals O1, O2, O3, O4, O5, O6, O7, and O8 that weighted the respective detection signals V1, V2, V3, V4, V5, V6, V7, and V8 of the plurality of photodetectors 52. The PC11 is configured to discriminate the generation position of the fluorescence S based on the addition signal Vo added by the weighting arithmetic circuit 55. As a result, the generation position of the fluorescence S can be discriminated only by adding the output signals O1, O2, O3, O4, O5, O6, O7, and O8 by the weighting arithmetic circuit 55, so that the configuration of the radiation detector 5 can be simplified.

Further, in the first embodiment, as described above, the weighting factor is set based on the weighting ratio set so that the weighting ratio at the end portion is greater than that of the weighting ratio on the central portion side. As a result, it is possible to improve the discrimination performance of the scintillator element 51a that gamma rays enter and fluorescence S is generated, and therefore, it is possible to improve the accuracy of the position signal correction, the energy correction, and the sensitivity-non-uniformity correction in the correction circuit 56.

Further, in the first embodiment, as described above, only the weighting of the plurality of photodetectors 52 of the respective detection signals V1, V2, V3, V4, V5, V6, V7, and V8 is adjusted. Since the construction of the radiation detector 5 is not changed, it becomes possible to suppress the generation of unwanted reflections and diffusions of the fluorescence S generated in cases where a light guide or a light partition is arranged. As a result, the deterioration of the temporal resolution of the PET apparatus 1 can be suppressed.

Second Embodiment

Next, with reference to FIG. 21 to FIG. 23, a second embodiment will be described. In this second embodiment, different from the first embodiment, an example will be described in which the weighting ratio on the central portion side is set to be. Note that in the drawings, the same configuration as that of the aforementioned first embodiment is denoted by the same reference symbol as that of the first embodiment, and the descriptions thereof are omitted.

In the weighting arithmetic circuit 55, as shown in FIG. 19, due to the fact that the photodetector 52 is optically connected to a plurality of scintillator elements 51a, not only the interval between the points at the end portions but also the interval between the points at the central portion become uneven in the two-dimensional map (see FIG. 22). Specifically, the interval between the points in the region A6 at the central portion shown in FIG. 19 is smaller than the interval between the points in the region A3 at the central portion shown in FIG. 13. At this time, as compared with the interval between the valley portions of the peak values in the region B3 at the central portion shown in FIG. 14, the interval between the valley portions of the peak values in the region B6 at the central portion shown in FIG. 20 is smaller than the interval between the peak values in the region B3 at the central portion shown in FIG. 14.

Therefore, in the weighting arithmetic circuit 55 of the second embodiment, as shown in FIG. 21, the weighting ratio is set so that the difference between the weighting ratios becomes constant not only at both end portions in the lateral direction but also on the central portion side. In addition, the difference between the weighting ratio at the end portion and the weighting ratio on the most end portion side between the weighting ratios on the central portion side is set to be greater than the difference between the other weighting ratios.

Specifically, the weighting ratio is (O2−O1):(O3−O2): (O4−O3):(O5−O4):(O6−O5):(O7−O6):(O8−O7)=10:2:3:2: 3:2:10. In this case, as to the weighting ratio, the difference between the weighting ratios on the central portion side is a constant value of 1. The weighting ratio described above can be determined based on simulations.

Here, the calculation of the resistance value is exemplified below using specific numerical values. The resistance values of the plurality of resistors R1, R2, R3, R4, R5, R6, R7, and R8 become R2=54 [Ω], R3=46 [Ω], R4=37.5 [Ω], R5=33 [Ω], R6=28 [Ω], R7=26 [Ω], and R8=18 [Ω], if the reference output signal is O1 and R1=600 [Ω] as examples. That is, based on the weighting ratio, since O2−O1 is 10×O1, O2 becomes 11×O1. Here, to make the output signal O2 eleven (11) times the output signal O1, the resistance value of the resistor R2 is set to 1/11 of the resistance value of the resistor R1. Therefore, R2=54 [Ω]. The resistor R3, resistor R4, resistor R5, resistor R6, resistor R7, and resistor R8 are calculated in the same manner.

Here, a two-dimensional map showing a two-dimensional array of the scintillator elements 51a is formed based on the addition signal Vo of the plurality of output signals O1, O2, O3, O4, O5, O6, O7, and O8. On the two-dimensional map, as shown in FIG. 22, the interval between the point showing the scintillator element 51a arranged at the end portion and the point showing the scintillator element 51a adjacent to the scintillator element 51a arranged at the end portion in the regions surrounded by A7 and A8 becomes close to the interval in the regions surrounded by A4 and A5. Further, on the two-dimensional map, the interval between the points showing the scintillator elements 51a arranged on the central portion side in the region surrounded by A9 is greater than the interval in the region surrounded by A6.

Further, based on the addition signal Vo of the plurality of output signals O1, O2, O3, O4, O5, O6, O7, and O8, a graph showing the relationship between the lateral positions of the scintillator elements 51a and the peak values of the energy signal values is formed. On the graph, as shown in FIG. 23, the interval of the valley portion between the peak value at the end portion and the peak value adjacent to the peak value at the end portion in the region surrounded by B7 and B8 becomes close to the interval in the region surrounded by B4 and B5. Further, on the graph, the interval between the valley portions of the peak-values at the central portion in the region surrounded by B9 is greater than the interval in the region surrounded by B6.

As described above, in the weighting arithmetic circuit 55, by changing the weighting ratio and adjusting the plurality of resistors, it is possible to suppress the deterioration of the calculation accuracy of the weighting arithmetic circuit 55 at the end portions (i.e., both end portions in lateral direction) and to suppress the deterioration of the calculation accuracy of the weighting arithmetic circuit 55 at the central portion. Note that the rest of the configuration of the second embodiment is the same as that of the first embodiment.

(Effects of Second Embodiment)

In this second embodiment, the following effects can be obtained.

In the second embodiment, as described above, the weighting ratio is set so that the difference between the weighting ratios of the adjacent photodetectors 52 other than those at the end portion is 1. As a result, it is possible to differentiate the weighted output signals O2, O3, O4, O5, O6, and O7 of the photodetectors 52 arranged on the central portion side, and thus it is also possible to differentiate the weighted signal values of the photodetectors 52 arranged on the central portion side. As a result, it is possible to prevent that the difference between the output signals O2, O3, O4, O5, O6, and O7 of the photodetectors 52 arranged on the central portion side becomes small since the difference between the respective output signals O1 and O8 of the photodetectors 52 arranged at the end portions and the output signals O2 and O7 of the photodetectors 52 adjacent to the photodetectors 52 arranged at the end portion is increased.

Further, in the second embodiment, as described above, the weighting is set so that the weighting ratio at the end portion is greater than the weighting ratio on the central portion side, and the difference between the weighting ratios of the adjacent photodetectors 52 other than those arranged at the end portions is 1. This makes it possible to differentiate the output signals O2, O3, O4, O5, O6, and O7 of the photodetectors 52 arranged on the central portion side in a state in which the difference between the output signal O1 of the photodetector 52 arranged at the end portion and the output signal O2 of the photodetector 52 adjacent to the photodetector 52 arranged at the end portion is increased. As a result, the performance of discriminating the plurality of scintillator elements 51a in the radiation detector 5 can be improved, and thus the spatial resolution of the PET apparatus 1 can be improved. The other effects of the second embodiment are the same as those of the first embodiment.

Modified Embodiment

It should be understood that the embodiments disclosed here are examples in all respects and are not restrictive. The scope of the present invention is shown by the claims rather than the descriptions of the embodiments described above and includes all changes (modifications) within the meaning of equivalent and the scope of claims.

For example, in the first embodiment and the second embodiment described above, the weighting ratio is determined based on simulations, but the present invention is not limited thereto. The weighting ratio may be obtained based on experiments or may be obtained by modifying the weighting ratio obtained by simulations by experiments.

In the first embodiment and the second embodiment described above, the resistor through which the reference output signal flows is 600 [Ω], but the present invention is not limited to this. The resistor through which the reference output signal flows may be other than 600 [Ω].

In the first embodiment and the second embodiment described above, the weighting of the weighting arithmetic circuit 55 connected to the photodetectors 52 arranged in the lateral direction is changed, but the present invention is not limited to this. The weighting of the weighting arithmetic circuit connected to the photodetectors arranged in the longitudinal direction may also be changed.

In the first embodiment and the second embodiment described above, although the weighting is performed on the detection signals V1, V2, V3, V4, V5, V6, V7, and V8 output from the photodetectors 52 in the weighting arithmetic circuit 55, the present invention is not limited to this. In the present invention, the weighting may be performed on the detection signal output from the photodetector in the PC (personal computer).

In the first embodiment and the second embodiment described above, although the nuclear medicine diagnostic device is a PET apparatus 1, the present invention is not limited to this. In the present invention, the nuclear medicine diagnostic device may be a SPECT (Single Photon Emission Computed Tomography) device.

In the first embodiment and the second embodiment described above, the photodetector 52 is composed of a photoelectron multiplier tube, but the present invention is not limited to this. In the present invention, the photodetector may be composed of a silicon photomultiplier.

In the first embodiment and the second embodiment described above, the plurality (12×6) of scintillator elements 51a is two-dimensionally arranged, but the present invention is not limited to this. For example, a plurality (15×6) of scintillator elements may be two-dimensionally arranged.

In the first embodiment and the second embodiment described above, the plurality (8×4) of photodetectors 52 is two-dimensionally arranged, but the present invention is not limited to this. For example, a plurality of (10×4) photodetectors 52 may be two-dimensionally arranged.

In the first embodiment and the second embodiment described above, no light guide is arranged between the scintillator 51 and the photodetector 52, but the present invention is not limited to this. A light guide may be arranged between the scintillator and the photodetector. For example, in cases where a light guide is arranged between the scintillator and the photodetector, the weighting ratio is preferably set to (O2−O1):(O3−O2):(O4−O3):(O5−O4): (O6−O5):(O7−O6):(O8−O7)=10:1:3:1:3:1:10.

In the first embodiment and the second embodiment described above, three pieces of scintillator elements 51a are optically connected to two pieces of photodetectors 52, but the present invention is not limited to this. For example, as shown in FIG. 24, five pieces of scintillator elements 351a may be optically connected to three pieces of photodetectors 352. In this case, for example, the weighting ratio is preferably set to (O2−O1):(O3−O2):(O4−O3):(O5−O4):(O6−O5)=10:3:5:3:10.

In the second embodiment described above, in the weighting ratio, the difference between the weighting ratios on the central portion side is 1, but the present invention is not limited to this. In the present invention, in the weighting ratio, the difference between the weighting ratios on the central portion side may be 2, or may be a value (e.g., 1.5) other than 1 or 2.

In the first embodiment and the second embodiment described above, in the weighting ration, the difference between the weighting ratios on the central portion side is constant, but the present invention is not limited to this. In the present invention, in the weighting ratio, the difference between the weighting ratios on the central portion side may be randomly determined.

DESCRIPTION OF SYMBOLS

1: PET apparatus (nuclear medicine diagnostic device)
5, 305: radiation detector
10: subject
11: PC (controller)
51, 351; scintillator
51a, 351a: scintillator element
52, 352: photodetector
55: weighting arithmetic circuit (adding circuit)
S: fluorescence

The invention claimed is:

1. A radiation detector comprising:
a scintillator in which a plurality of scintillator elements that convert radiation into fluorescence is arranged;
a plurality of photodetectors connected to the plurality of scintillator elements, the plurality of photodetectors whose number is less than a number of the plurality of scintillator elements being arranged, and each photodetector being configured to detect fluorescence generated in the scintillator element; and
a controller configured to specify a generation position of the fluorescence based on signal values of the plurality of photodetectors, the signal values being obtained by weighting respective detection signals of the plurality of photodetectors,
wherein weighting of the detection signal of the photodetector arranged on an end portion side between the plurality of photodetectors is set to be greater than weighting of the detection signals of photodetectors arranged on a central portion side between the plurality of photodetectors, and
wherein the weighting is based on a weighting ratio based on a difference between the signal values of weighted detection signals of the photodetectors arranged adjacently, and is set such that the weighting ratio at the end portion side is greater than the weighting ratio on the central portion side.

2. The radiation detector as recited in claim 1,
wherein a difference between the weighting ratio at the end portion and the weighting ratio on a most end portion side among weighting ratios on the central portion side is set to be greater than differences between weighting ratios other than those at the end portion.

3. The radiation detector as recited in claim 2,
wherein the weighting ratio is set so that the difference between the weighting ratios other than those at the end portion is a constant value of 1 or 2.

4. The radiation detector as recited in claim 2, further comprising:
a plurality of resistors for weighting respective detection signals output from the plurality of photodetectors,
wherein resistance values of the plurality of resistors are adjusted based on the weighting ratio.

5. The radiation detector as recited in claim 4, further comprising:
an adding circuit configured to add the weighted signal value to respective detection signals of the plurality of photodetectors,
wherein the controller is configured to specify the generation position of the fluorescence based on the signal value added by the adding circuit.

* * * * *